US008077873B2

(12) United States Patent
Shridhar et al.

(10) Patent No.: US 8,077,873 B2
(45) Date of Patent: Dec. 13, 2011

(54) SYSTEM FOR ACTIVE NOISE CONTROL WITH ADAPTIVE SPEAKER SELECTION

(75) Inventors: Vasant Shridhar, Royal Oak, MI (US); Duane Wertz, Byron, MI (US)

(73) Assignee: Harman International Industries, Incorporated, Northridge, CA (US)

( * ) Notice: Subject to any disclaimer, the term of this patent is extended or adjusted under 35 U.S.C. 154(b) by 301 days.

(21) Appl. No.: 12/466,282

(22) Filed: May 14, 2009

(65) Prior Publication Data

US 2010/0290635 A1 Nov. 18, 2010

(51) Int. Cl.
*A61F 11/06* (2006.01)

(52) U.S. Cl. ........................................ 381/71.1; 381/302

(58) Field of Classification Search ................. 381/71.1, 381/71.4, 302, 94.1

See application file for complete search history.

(56) References Cited

U.S. PATENT DOCUMENTS 4,589,137 A 5/1986 Miller ............................ 381/94
4,628,156 A 12/1986 Irvin ............................ 379/410
4,654,871 A 3/1987 Chaplin et al. .................. 381/71
4,677,678 A 6/1987 McCutchen .................... 381/72
4,910,799 A 3/1990 Takayama ..................... 455/296
4,941,187 A 7/1990 Slater ............................ 381/86
4,947,356 A 8/1990 Elliot et al.
4,953,217 A 8/1990 Twiney et al. .................. 381/72
4,977,600 A 12/1990 Ziegler ........................... 381/71
4,985,925 A 1/1991 Langberg et al. ............... 381/72
4,998,241 A 3/1991 Brox et al. ................... 370/32.1
5,001,763 A 3/1991 Moseley ......................... 381/71
5,033,082 A 7/1991 Eriksson et al. .............. 379/410
5,091,954 A 2/1992 Sasaki et al. .................... 381/72
5,105,377 A 4/1992 Ziegler, Jr. ............... 364/724.01
5,133,017 A 7/1992 Cain et al. ....................... 381/71
5,138,664 A 8/1992 Kimura et al. .................. 381/72
5,170,433 A 12/1992 Elliot et al.
5,182,774 A 1/1993 Bourk ............................ 381/71
5,208,868 A 5/1993 Sapiejewski .................. 381/183
5,251,262 A * 10/1993 Suzuki et al. ................ 381/71.8
5,276,740 A 1/1994 Inanaga et al. ................ 381/187
5,289,147 A 2/1994 Koike et al. ................... 355/200
5,305,387 A 4/1994 Sapiejewski .................... 381/71
5,337,366 A 8/1994 Eguchi et al. .................. 381/71

(Continued)

FOREIGN PATENT DOCUMENTS

CN 1688179 A 10/2005

(Continued)

OTHER PUBLICATIONS

Gao, F. X. Y. et al., "An Adaptive Backpropagation Cascade IIR Filter," *IEEE*, vol. 39, No. 9, 1992, pp. 606-610.

(Continued)

*Primary Examiner* — Patricia Nguyen

(74) *Attorney, Agent, or Firm* — Brinks Hofer Gilson & Lione

(57) ABSTRACT

An active noise control system generates an anti-noise signal to drive a first speaker group including at least one speaker to produce sound waves to destructively interfere with an undesired sound in at least one quiet zone. The active noise control system receives error signals representative of a combination of undesired sound and destructively interfering sound waves produced by the first speaker group. The active noise control system may select a second speaker group to replace the first speaker group based on the error signals.

22 Claims, 9 Drawing Sheets

U.S. PATENT DOCUMENTS

| | | | | |
|---|---|---|---|---|
| 5,371,802 | A | 12/1994 | McDonald et al. | |
| 5,377,276 | A | 12/1994 | Terai et al. | 381/71 |
| 5,381,473 | A | 1/1995 | Andrea et al. | 379/387 |
| 5,381,485 | A | 1/1995 | Elliot | |
| 5,400,409 | A | 3/1995 | Linhard | 381/92 |
| 5,427,102 | A | 6/1995 | Shimode et al. | 128/653.2 |
| 5,485,523 | A | 1/1996 | Tamamura et al. | 381/71 |
| 5,492,129 | A | 2/1996 | Greenberger | 128/715 |
| 5,493,616 | A * | 2/1996 | Iidaka et al. | 381/71.4 |
| 5,497,426 | A | 3/1996 | Jay | 381/67 |
| 5,499,302 | A * | 3/1996 | Nagami et al. | 381/71.4 |
| 5,526,421 | A | 6/1996 | Berger et al. | 379/389 |
| 5,559,893 | A | 9/1996 | Krokstad et al. | 381/71 |
| 5,586,189 | A | 12/1996 | Allie et al. | 381/71 |
| 5,602,927 | A | 2/1997 | Tamamura et al. | 381/71 |
| 5,602,928 | A | 2/1997 | Eriksson et al. | 381/71 |
| 5,604,813 | A | 2/1997 | Evans et al. | 381/71 |
| 5,621,803 | A | 4/1997 | Laak | 381/71 |
| 5,673,325 | A | 9/1997 | Andrea et al. | 381/92 |
| 5,675,658 | A | 10/1997 | Brittain | 381/72 |
| 5,680,337 | A | 10/1997 | Pedersen et al. | 364/724.19 |
| 5,687,075 | A | 11/1997 | Stothers | |
| 5,691,893 | A | 11/1997 | Stothers | |
| 5,692,059 | A | 11/1997 | Kruger | 381/151 |
| 5,699,437 | A | 12/1997 | Finn | |
| 5,706,344 | A | 1/1998 | Finn | 379/410 |
| 5,715,320 | A | 2/1998 | Allie et al. | 381/71.12 |
| 5,727,066 | A | 3/1998 | Elliott et al. | |
| 5,737,433 | A | 4/1998 | Gardner | 381/94.7 |
| 5,740,257 | A | 4/1998 | Marcus | 381/71.6 |
| 5,745,396 | A | 4/1998 | Shanbhag | 364/724.19 |
| 5,768,124 | A | 6/1998 | Stothers et al. | |
| 5,774,564 | A | 6/1998 | Eguchi et al. | 381/71.11 |
| 5,774,565 | A | 6/1998 | Benning et al. | 381/83 |
| 5,809,156 | A | 9/1998 | Bartels et al. | 381/183 |
| 5,815,582 | A | 9/1998 | Claybaugh et al. | 381/71.6 |
| 5,872,728 | A | 2/1999 | Ritcher | 364/724.2 |
| 5,937,070 | A | 8/1999 | Todter et al. | 381/71.6 |
| 6,069,959 | A | 5/2000 | Jones | 381/71.6 |
| 6,078,672 | A | 6/2000 | Saunders et al. | 381/71.6 |
| 6,163,610 | A | 12/2000 | Bartlett et al. | 379/433 |
| 6,166,573 | A | 12/2000 | Moore et al. | 327/161 |
| 6,181,801 | B1 | 1/2001 | Puthuff et al. | 381/380 |
| 6,185,299 | B1 | 2/2001 | Goldin | 379/406 |
| 6,278,785 | B1 | 8/2001 | Thomasson | 381/66 |
| 6,295,364 | B1 | 9/2001 | Finn et al. | 381/110 |
| 6,301,364 | B1 | 10/2001 | Lowmiller et al. | 381/66 |
| 6,343,127 | B1 | 1/2002 | Billoud | 381/71.4 |
| 6,347,146 | B1 | 2/2002 | Short et al. | 381/15 |
| 6,377,680 | B1 | 4/2002 | Foladare et al. | 379/392.01 |
| 6,421,443 | B1 | 7/2002 | Moore et al. | 379/406.01 |
| 6,445,799 | B1 | 9/2002 | Taenzer et al. | 381/71.6 |
| 6,445,805 | B1 | 9/2002 | Grugel | 381/330 |
| 6,466,673 | B1 | 10/2002 | Hardy | |
| 6,496,581 | B1 | 12/2002 | Finn et al. | 379/406.01 |
| 6,505,057 | B1 | 1/2003 | Finn et al. | 455/569 |
| 6,529,605 | B1 | 3/2003 | Christoph | |
| 6,532,289 | B1 | 3/2003 | Magid | 379/406.01 |
| 6,532,296 | B1 * | 3/2003 | Vaudrey et al. | 381/371 |
| 6,567,524 | B1 | 5/2003 | Svean et al. | 381/71.1 |
| 6,567,525 | B1 | 5/2003 | Sapiejewski | 381/71.6 |
| 6,597,792 | B1 | 7/2003 | Sapiejewski et al. | 381/71.6 |
| 6,625,286 | B1 | 9/2003 | Rubacha et al. | 381/93 |
| 6,633,894 | B1 | 10/2003 | Cole | 708/300 |
| 6,643,619 | B1 | 11/2003 | Linhard et al. | 704/233 |
| 6,665,410 | B1 | 12/2003 | Parkins | 381/71.1 |
| 6,687,669 | B1 | 2/2004 | Schrogmeier et al. | 704/226 |
| 6,690,800 | B2 | 2/2004 | Resnick | 381/73.1 |
| 6,798,881 | B2 | 9/2004 | Thomasson | 379/406.07 |
| 6,845,162 | B1 | 1/2005 | Emborg et al. | 381/71.4 |
| 6,991,289 | B2 | 1/2006 | House | 297/217.4 |
| 7,020,288 | B1 | 3/2006 | Ohashi | 381/71.4 |
| 7,062,049 | B1 * | 6/2006 | Inoue et al. | 381/71.4 |
| 7,103,188 | B1 | 9/2006 | Jones | 381/71.9 |
| 7,133,529 | B2 | 11/2006 | Ura | 381/66 |
| 7,333,618 | B2 | 2/2008 | Shuttleworth et al. | 381/57 |
| 7,440,578 | B2 | 10/2008 | Arai et al. | 381/302 |
| 7,469,051 | B2 | 12/2008 | Sapashe et al. | 381/104 |
| 7,574,006 | B2 * | 8/2009 | Funayama et al. | 381/71.12 |
| 7,627,352 | B2 | 12/2009 | Gauger, Jr. et al. | 455/569.1 |
| 7,630,432 | B2 | 12/2009 | Hofmeister | 375/232 |
| 7,773,760 | B2 | 8/2010 | Sakamoto et al. | 381/71.9 |
| 7,808,395 | B2 | 10/2010 | Raisanen et al. | 340/667 |
| 7,873,173 | B2 | 1/2011 | Inoue et al. | 381/71.4 |
| 7,885,417 | B2 | 2/2011 | Christoph | 381/71.11 |
| 7,933,420 | B2 | 4/2011 | Copley et al. | 381/71.11 |
| 2001/0036283 | A1 | 11/2001 | Donaldson | 381/71.11 |
| 2002/0068617 | A1 | 6/2002 | Han | |
| 2002/0076059 | A1 | 6/2002 | Joynes | 381/71.6 |
| 2002/0138263 | A1 | 9/2002 | Deligne et al. | 704/233 |
| 2002/0143528 | A1 | 10/2002 | Deligne et al. | 704/224 |
| 2002/0172374 | A1 | 11/2002 | Bizjak | 381/71.14 |
| 2002/0176589 | A1 | 11/2002 | Buck et al. | 381/94.7 |
| 2003/0035551 | A1 | 2/2003 | Light et al. | 381/71.6 |
| 2003/0103636 | A1 | 6/2003 | Arai et al. | 381/302 |
| 2003/0142841 | A1 | 7/2003 | Wiegand | 381/172 |
| 2003/0228019 | A1 | 12/2003 | Eichler et al. | 381/71.8 |
| 2004/0037429 | A1 | 2/2004 | Candioty | 381/67 |
| 2004/0076302 | A1 | 4/2004 | Christoph | 381/57 |
| 2005/0175187 | A1 | 8/2005 | Wright et al. | 381/71.12 |
| 2005/0207585 | A1 | 9/2005 | Christoph | 381/71.11 |
| 2005/0226434 | A1 | 10/2005 | Franz et al. | 381/71.7 |
| 2005/0232435 | A1 | 10/2005 | Stothers et al. | |
| 2006/0098809 | A1 | 5/2006 | Nongpiur et al. | 379/406.14 |
| 2006/0153394 | A1 | 7/2006 | Beasley | 381/57 |
| 2006/0251266 | A1 | 11/2006 | Saunders et al. | 381/71.1 |
| 2006/0262935 | A1 | 11/2006 | Goose et al. | 381/17 |
| 2007/0053532 | A1 | 3/2007 | Elliot et al. | |
| 2007/0098119 | A1 | 5/2007 | Stothers et al. | |
| 2007/0253567 | A1 | 11/2007 | Sapiejewski | 381/71.6 |
| 2008/0095383 | A1 | 4/2008 | Pan et al. | 381/71.11 |
| 2008/0181422 | A1 | 7/2008 | Christoph | 381/73.1 |
| 2008/0192948 | A1 | 8/2008 | Kan et al. | 381/71.4 |
| 2008/0247560 | A1 | 10/2008 | Fukuda et al. | 381/71.6 |
| 2009/0067638 | A1 | 3/2009 | Sakamoto et al. | 381/71.4 |
| 2009/0086990 | A1 | 4/2009 | Christoph | 381/71.12 |
| 2009/0086995 | A1 | 4/2009 | Christoph et al. | |
| 2009/0220102 | A1 | 9/2009 | Pan et al. | 381/71.11 |
| 2010/0014685 | A1 | 1/2010 | Wurm | 381/71.11 |
| 2010/0061566 | A1 | 3/2010 | Moon et al. | 381/71.8 |
| 2010/0098263 | A1 | 4/2010 | Pan et al. | 381/71.11 |
| 2010/0098265 | A1 | 4/2010 | Pan et al. | 381/94.1 |
| 2010/0124336 | A1 | 5/2010 | Shridhar et al. | 371/71.4 |
| 2010/0124337 | A1 | 5/2010 | Wertz et al. | 371/71.11 |
| 2010/0177905 | A1 | 7/2010 | Shridhar et al. | 381/71.11 |
| 2010/0226505 | A1 | 9/2010 | Kimura | 381/71.6 |
| 2010/0239105 | A1 | 9/2010 | Pan | 381/94.9 |
| 2010/0260345 | A1 | 10/2010 | Shridhar et al. | 381/71.1 |
| 2010/0266134 | A1 | 10/2010 | Wertz et al. | 381/71.1 |
| 2010/0266137 | A1 | 10/2010 | Sibbald et al. | 381/71.6 |
| 2010/0272275 | A1 | 10/2010 | Carreras et al. | |
| 2010/0272280 | A1 | 10/2010 | Joho et al. | 381/71.6 |
| 2010/0272281 | A1 | 10/2010 | Carreras et al. | 381/71.6 |
| 2010/0274564 | A1 | 10/2010 | Bakalos et al. | 704/500 |
| 2010/0296669 | A1 | 11/2010 | Oh et al. | 381/109 |
| 2011/0116643 | A1 | 5/2011 | Tiscareno et al. | 381/58 |

FOREIGN PATENT DOCUMENTS

| | | | |
|---|---|---|---|
| EP | 0 622 779 | A2 | 11/1994 |
| EP | 0 539 940 | B1 | 4/1996 |
| EP | 0 572 492 | B1 | 11/1997 |
| EP | 1 577 879 | B1 | 7/2008 |
| EP | 1 947 642 | A1 | 7/2008 |
| GB | 2 293 898 | B | 4/1996 |
| JP | 11 259078 | A | 9/1999 |
| WO | WO 90/09655 | | 8/1990 |
| WO | WO 94/09480 | | 4/1994 |
| WO | WO 94/09481 | | 4/1994 |
| WO | WO 94/09482 | | 4/1994 |
| WO | WO 95/26521 | | 10/1995 |
| WO | WO 96/10780 | | 4/1996 |

OTHER PUBLICATIONS

Kuo, S. M. et al., "Active Noise Control Systems: Algorithms and DSP Implementations," John Wiley & Sons, Inc., New York, NY, Copyright 1996, pp. 88-97.

Extended European Search Report from European Application No. EP 10150426.4-2213, dated May 26, 2010, 7 pgs.
Martins C R et al., "Fast Adaptive Noise Canceller Using the LMS Algorithm", Proceedings of the International Conference on Signal Processing Applications and Technology, vol. 1, Sep. 28, 1993, 8 pgs.
European Search Report from European Application No. EP 10162225, dated Oct. 1, 2010, 5 pgs.
Gonzalez, A. et al., "Minimisation of the maximum error signal in active control", IEEE International Conference on Acoustics, Speech, and Signal Processing, 1997, 4 pgs.
Kuo, S. M. et al., "Active Noise Conirol Systems: Algorithms and DSP Implementations," John Wiley & Sons, Inc., New York, NY, Copyright 1996, 419 pgs.
Colin H. Hansen et al., "Active Control of Noise and Vibration," E & FN Spon., London SE1, Copyright 1997, pp. 642-652.
Office Action, dated Aug. 26, 2011, pp. 1-24, U.S. Appl. No. 12/421,459, U.S. Patent and Trademark Office, Virginia.
Office Action, dated Jul. 25, 2011, pp. 1-11, U.S. Appl. No. 12/275,118, U.S. Patent and Trademark Office, Virginia.
Office Action, dated Aug. 3, 2011, pp. 1-33, U.S. Appl. No. 12/352,435, U.S. Patent and Trademark Office, Virginia.
Office Action, dated Aug. 17, 2011, pp. 1-26, U.S. Appl. No. 12/425,997, U.S. Patent and Trademark Office, Virginia.
Office Action, dated Sep. 13, 2011, pp. 1-16, U.S. Appl. No. 12/420,658, U.S. Patent and Trademark Office, Virginia.
Chen, Kean et al., Adaptive Active Noise Elimination and Filter-XLMS Algorithm, 1993, pp. 27-33, vol. 12 (4), Applied Acoustics, and translation of Abstract (8 pgs.).

* cited by examiner

SYSTEM FOR ACTIVE NOISE CONTROL WITH ADAPTIVE SPEAKER SELECTION

BACKGROUND OF THE INVENTION

1. Technical Field

This invention relates to active noise control, and more specifically to automatic selection of speaker combinations to produce destructively interfering sound waves.

2. Related Art

Active noise control may be used to generate sound waves or "anti noise" that destructively interferes with undesired sound waves. The destructively interfering sound waves may be produced through a loudspeaker to combine with the undesired sound waves in an attempt to cancel the undesired noise. Combination of the destructively interfering sound waves and the undesired sound waves can eliminate or minimize perception of the undesired sound waves by one or more listeners within a listening space.

An active noise control system generally includes one or more microphones to detect sound within an area that is targeted for destructive interference. The detected sound is used as a feedback error signal. The error signal is used to adjust an adaptive filter included in the active noise control system. The filter generates an anti-noise signal used to create destructively interfering sound waves through at least one speaker. The filter is adjusted to adjust the destructively interfering sound waves in an effort to optimize cancellation within the area. In systems having multiple speakers, a fixed number of speakers may be used to generate anti-noise. However, some speakers may not be used to generate anti-noise but in some situations may be more suitable than speakers being used due to source location and characteristics of the undesired sound. In addition, the source location and characteristics of the undesired sound may change over the course of time. Therefore, a need exists to adaptively select speakers being used to produce destructively-interfering sound waves.

SUMMARY

An active noise control (ANC) system may generate one or more anti-noise signals to drive one or more respective speakers. The speakers may be driven to generate sound waves to destructively interfere with undesired sound present in one or more quiet zones within a listening space. The ANC system may generate the anti-noise signals based on input signals representative of the undesired sound.

The ANC system may include any number of anti-noise generators each capable of generating an anti-noise signal. Each of the anti-noise generators may include one or more learning algorithm units (LAU) and adaptive filters. The LAU may receive error signals in the form of sensor input signals from sensors such as microphones positioned in each of the quiet zones.

One or more speakers within an audio system containing multiple speakers may be selected to be actively driven by a respective anti-noise signal. Combination of sound waves produced by the actively-driven selected speakers and the undesired sound in each quiet zone may result in an error signal generated by each sensor for each corresponding quiet zone. The ANC system may select particular speakers to produce anti-noise sound waves for predetermined amounts of time along with the actively-driven speakers to determine if error signals are reduced. If a reduction in error signals is present, the selected particular speakers may permanently replace one or more of the actively-driven speakers.

The ANC system may also be configured to simulate sound wave production based on the anti-noise signals from one or more of the other speakers in the audio system that are not being actively-driven to produce sound waves. The simulated sound wave production may be used to determine a simulated effect on at least one of the error signals. The ANC system may compare the simulated effect on the error signals to the actual error signals. Based on the comparison, the ANC system may select one or more speakers in the audio system from the simulation to be actively-driven in addition to, or instead of, the speakers being actively driven.

The ANC system may simulate production of sound waves from various speaker combinations including one or more speakers not currently being actively driven. Results based on a simulated effect of each simulated speaker combination on the error signals may be compared to select a speaker combination for comparison to the actively-driven speakers. The ANC system may replace the actively-driven speakers with the selected speaker combination to be actively-driven.

The ANC system may analyze the characteristics of undesired sound in selecting speakers to be actively driven. The ANC system may determine a direction of propagation of undesired sound. The ANC system may select one or more speakers based on the direction of undesired sound. The ANC system may simulate production of anti-noise sound waves by the selected speaker or speakers.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

An active noise control (ANC) system is configured to generate destructively interfering sound waves to create one or more quiet zones. In general, this is accomplished by first determining the presence of an undesired sound and generating a destructively interfering sound wave. A destructively interfering sound wave may be included as part of a speaker output from a speaker. Each speaker may include one or more transducers configured to convert electrical signals into sound waves representative of the received electrical signals. A sensor, such as a microphone, in each quiet zone may receive the undesired sound and sound waves from a loudspeaker driven with the speaker output. Each microphone may include one or more transducers configured to detect sound waves and convert the detected sound waves to representative electrical signals. The sensors may each generate an output signal based on the received sound waves. The output signals may represent an error signal indicative of sound waves resulting from a combination of the undesired sound and the destructively interfering sound wave.

The ANC system may be configured to drive any combination of one or more available speakers to generate destructively interfering sound waves. The ANC system may be configured to select a first combination of speakers to be driven. Based on the error signals resulting from a combination of undesired sound and destructively interfering sound waves from the first combination, the ANC system may select a different combination of speakers to more accurately cancel undesired sound.

The ANC system may be configured to implement a simulator. The simulator may receive the error signals and a signal representative of the undesired sound to simulate production of destructively interfering signals by speaker combinations different from a speaker combination being actively used. The simulations may generate a simulated effect on the error signals. The ANC system may change the speaker combination based on the simulation results. The ANC may also change speaker combinations based on the direction of undesired sound.

As used herein, the term "quiet zone" or "listening region" refers to a three-dimensional area of space within which perception by a listener of an undesired sound is substantially reduced due to destructive interference by combination of sound waves of the undesired sound and anti-noise sound waves generated by one or more speakers. For example, the undesired sound may be reduced by approximately half, or 3 dB down within the quiet zone. In another example, the undesired sound may be reduced in magnitude to provide a perceived difference in magnitude of the undesired sound to a listener. In still another example, the undesired sound may be minimized as perceived by a listener.

Figure 1:
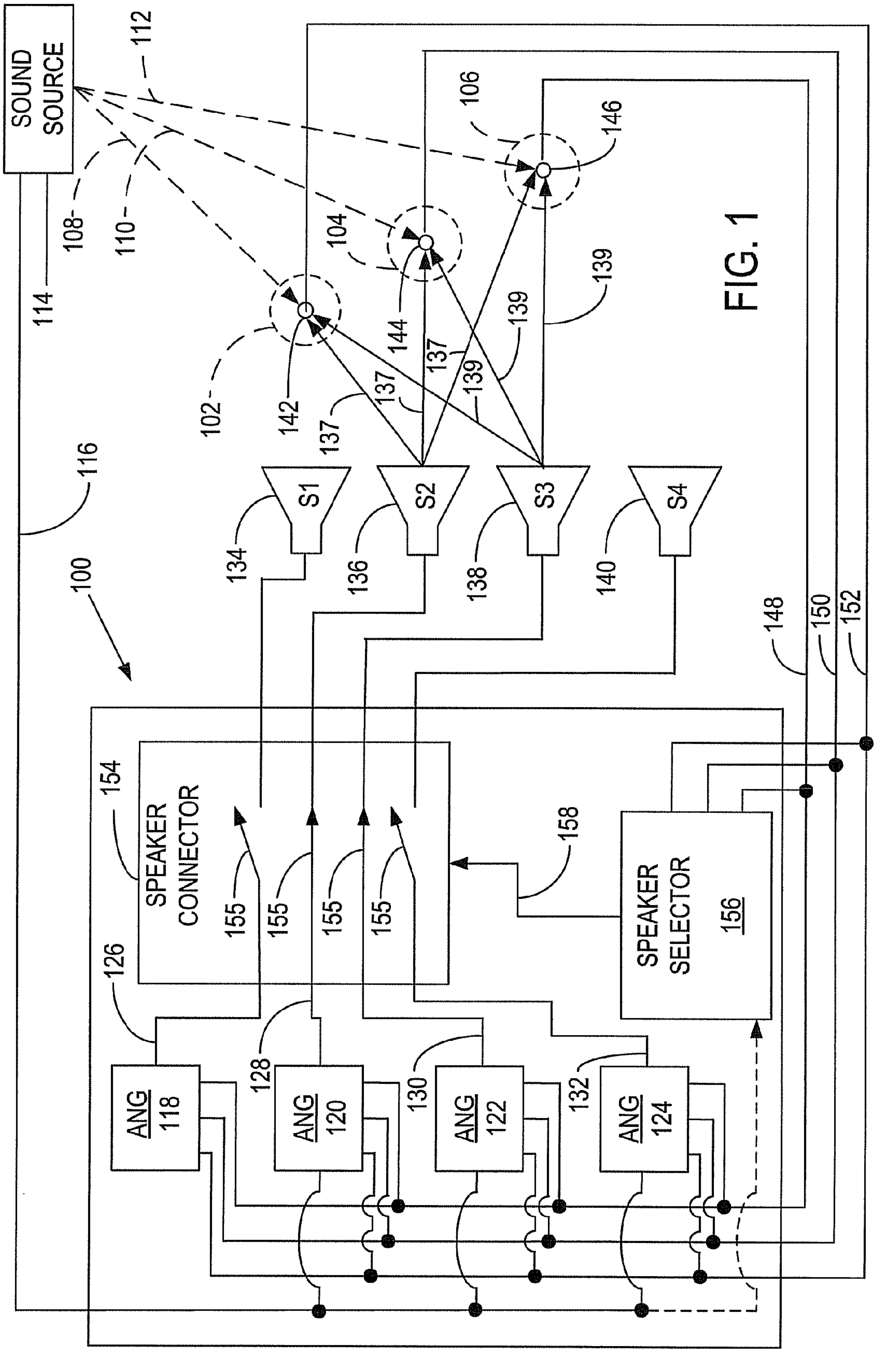
FIG. 1 is a diagrammatic view of an example active noise cancellation (ANC) system.

FIG. 1 is a diagrammatic example of an active noise control (ANC) system 100. The ANC system 100 may be implemented in various listening areas, such as a vehicle interior, to reduce or eliminate a particular sound frequency or frequency ranges from being audible in quiet zones 102, 104, and 106 or listening regions within the listening area. The example ANC system 100 of FIG. 1 is configured to generate signals at one or more desired frequencies or frequency ranges that may be generated as sound waves to destructively interfere with undesired sound, represented by dashed-arrows 108, 110, and 112 in FIG. 1, originating from a sound source 114. In one example, the ANC system 100 may be configured to destructively interfere with undesired sound within a frequency range of approximately 20-500 Hz. The ANC system 100 may receive an undesired sound signal 116 representative of sound emanating from the sound source 114 that may be audible in each of the quiet zones 102, 104, and 106.

The ANC system 100 may be configured to include a plurality of anti-noise generators. In FIG. 1, the ANC system 100 includes four anti-noise generators (ANG) 118, 120, 122, and 124. The ANC system 100 may be configured to include additional or fewer anti-noise generators than that shown in FIG. 1. Each anti-noise generator 118, 120, 122, and 124 may be configured to generate a respective anti-noise signal 126, 128, 130, and 132. Each anti-noise signal 126, 128, 130, and 132 may be used to drive at least one respective speaker 134, 136, 138, and 140. Thus, in other examples, one anti-noise generator may be configured to drive all or several speakers used with the ANC system 100. In one example the anti-noise signals 126, 128, 130, and 132 may ideally be representative of sound waves of approximately equal amplitude and frequency that are approximately 180 degrees out of phase with the undesired sound 108, 110, and 112 present in each of the quiet zones 102, 104, and 106, respectively. The 180 degree phase difference between the anti-noise signals 126, 128, 130, and 132 and the detected undesired sound may cause desirable destructive interference with the undesired sound in a respective area within the quiet zones 102, 104, and 106 in which the anti-noise sound waves produced by the speakers 134, 136, 138, and 140 and sound waves of the undesired sound 108, 110, and 112 destructively combine. The desirable destructive interference results in cancellation of the undesired sound within the respective quiet zones 102, 104, and 106, as perceived by a listener. In FIG. 1, each speaker 134, 136, 138, and 140 may produce sound waves based on the respective anti-noise signals 126, 128, 130, and 132 to destructively interfere with the undesired sound present in each of the quiet zones 102, 104, and 106.

A sensor such as microphones 142, 144, and 146, or any other devices or mechanisms for sensing audible sound waves may be placed in each of the quiet zones 102, 104, and 106, respectively. Each microphone 142, 144, and 146 may detect sound waves present in the respective quiet zones 102, 104, and 106. Each microphone 142, 144, and 146 may generate a respective output signal 148, 150, and 152, each representative of the detected sound waves within the respective quiet zones 102, 104, and 106. Each output signal 148, 150, 152 may be considered an error signal in that each output signal 148, 150, and 152 may represent the residual undesired sound following destructive interference of the anti-noise sound waves with the undesired sound 108, 110, and 112 in the quiet zones 102, 104, and 106, respectively.

In FIG. 1, the ANC system 100 may receive the error signals 148, 150, and 152. Each anti-noise generator 118, 120, 122, and 124 may receive the error signals 148, 150, and 152 and adjust the respective anti-noise signal 126, 128, 130, and 132 based on the error signal 148, 150, 152 in order to more accurately produce anti-noise sound waves to cancel the undesired sound. The ANC system 100 may be configured as a 2-channel system in which only two of the speakers 134, 136, 138, and 140 are "active," i.e., being driven by an anti-noise signal. In FIG. 1, the ANC system 100 includes a speaker connector 154 configured to provide the particular speakers 134, 136, 138, and 140 with the respective anti-noise signal 126, 128, 130, and 132. In the 2-channel arrangement with speakers 136 and 138 being active, the speaker 136 may produce sound waves 137 that propagate into each of the quiet zones 102, 104, and 106, respectively. Similarly, the active speaker 138 may produce sound waves 139 that propagate into each of the quiet zones 102, 104, and 106, respectively. In FIG. 1, switches 155 illustrate the ability of the speaker connector 154 to selectively allow the anti-noise signals 126, 128, 130, and 132 to drive the respective speakers 134, 136, 138, and 140. Although illustrated as a switch, in other examples, other forms of activating some of the speakers are possible, such as disabling processing of the anti-noise generators not being used.

The ANC system 100 may include a speaker selector 156. The speaker selector 156 may be configured to select one or more speakers to produce anti-noise sound waves not currently being used to produce anti-noise sound waves. In one example, the speaker selector 156 may be configured to select one or more speakers to produce anti-noise sound waves for a predetermined amount of time in addition to the active speakers already producing anti-noise sound waves. The speaker selector 156 may receive the error signals 148, 150, and 152. As each additional speaker produces anti-noise sound waves, the speaker selector 156 may determine if one or more of the error signals 148, 150, and 152 decreases. When the speaker selector 156 determines there is a decrease in error, the speaker selector 156 identifies the additional speaker causing the decrease in error. Upon identification, the speaker selector 156 may cease allowing anti-noise sound waves to be produced by the additional speakers. The speaker selector 156 may begin replacing each active speaker with the additional speaker to determine which active speaker should be replaced. Once the speaker for replacement is identified, the speaker selector 156 may generate a speaker selection signal 158 to the speaker connector 154. The speaker selection signal 158 may indicate the particular speakers 134, 136, 138, and 140 to receive the respective anti-noise signal 126, 128, 130, 132, respectively. In FIG. 1, switches 155 illustrate the ability of the speaker connector 154 to provide each anti-noise signal to the respective speaker. However, the anti-noise signals may be provided in various manners, such as enabling and disabling the ANGs 118, 120, 122, and 124.

In another example, the speaker selector 156 may simulate production from non-active speakers internally to recreate the anti-noise generators 118, 120, 122, and 124 and production of the corresponding anti-noise signals 126, 128, 130, and 132. The speaker selector 156 may be configured to simulate production of anti-noise sound waves from speaker combinations other than the currently-active speakers being currently implemented by the ANC system 100. For example, in FIG. 1, the speakers 136 and 138 are shown as being the two speakers being active and driven by the respective anti-noise signals 128 and 130. The speaker selector 156 may receive the error signals 148, 150, and 152 and the undesired sound signal 116. Using these signals, the speaker selector 156 may simulate the effect on the error signals 148, 150, and 152 of driving one of the speakers 136 and 138 with the respective anti-noise signal 126 and 132 instead of either of the speakers 134 or 140 or in addition to the speakers 134 and 140.

The speaker selector 156 may determine that addition of one or both of the speakers 134 and 140 may reduce at least one of the error signals 148, 150, and 152. If the speaker selector 156 determines that using one or both of speakers 134 and 140 will reduce at least one of the error signals 148, 150, and 152, the speaker selector 156 may provide a speaker configuration signal 158 to the speaker connector 154. The speaker connector 154 may adjust the particular speakers 134, 136, 138, and 140 to be driven by the respective anti-noise signal 126, 128, 130, and 132. For example, if the speaker selector 156 determines that driving speaker 134 instead of the speaker 136 will reduce at least one of the error signals 148, 150, and 152, the speaker selector 156 may indicate to the speaker connector 154 through the speaker configuration signal 158 prevention of the speaker 136 from being driven by the anti-noise signal 128 and to allow the speaker 134 to be driven by the anti-noise signal 130.

In alternative configurations, the ANC system 100 may be configured for more than 2 channels allowing the speaker selector 156 to determine the addition of more than one speaker. For example, the speaker selector 156 may determine that driving all speakers 134, 136, 138, and 140 may provide the most suitable combination for reducing the error signals 148, 150, and 152 and may indicate such combination to the speaker connector 154. In other alternative configurations, the ANC system 100 may be a single channel system, where only one of the speakers 134, 136, 138, and 140 may be used to generate anti-noise sound waves at any one time.

In alternative examples, the ANC system may be configured to implement a single anti-noise generator, such as the anti-noise generators 118, 120, 122, and 124. In a single anti-noise generator arrangement, each speaker 134, 136, 138, and 140 may be configured to selectively receive the same anti-noise signal generated from the single anti-noise generator based on a particular combination currently selected with the speaker connector 154.

Figure 2:
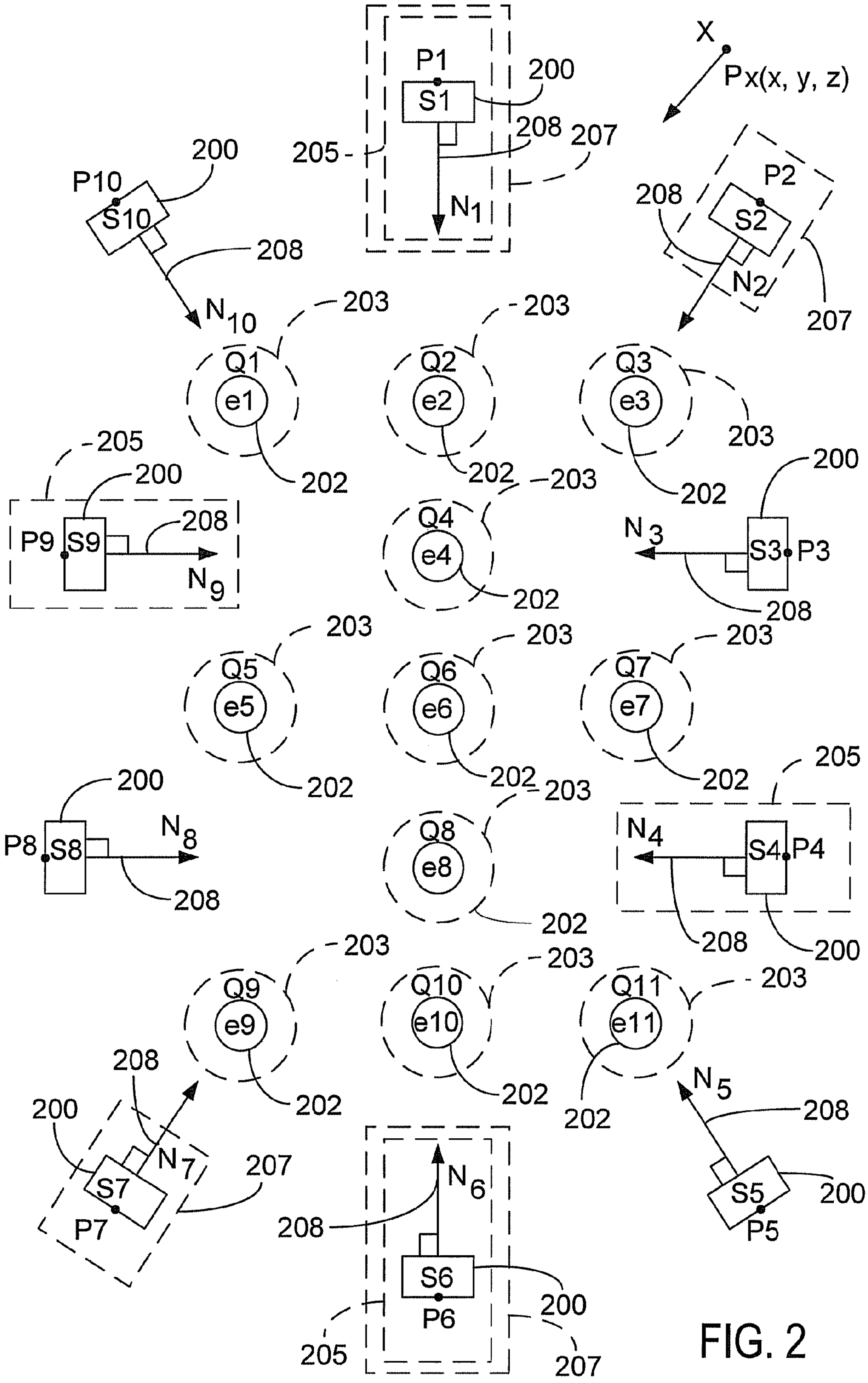
FIG. 2 is a diagrammatic view of an example speaker and microphone configuration.
Figure 3:
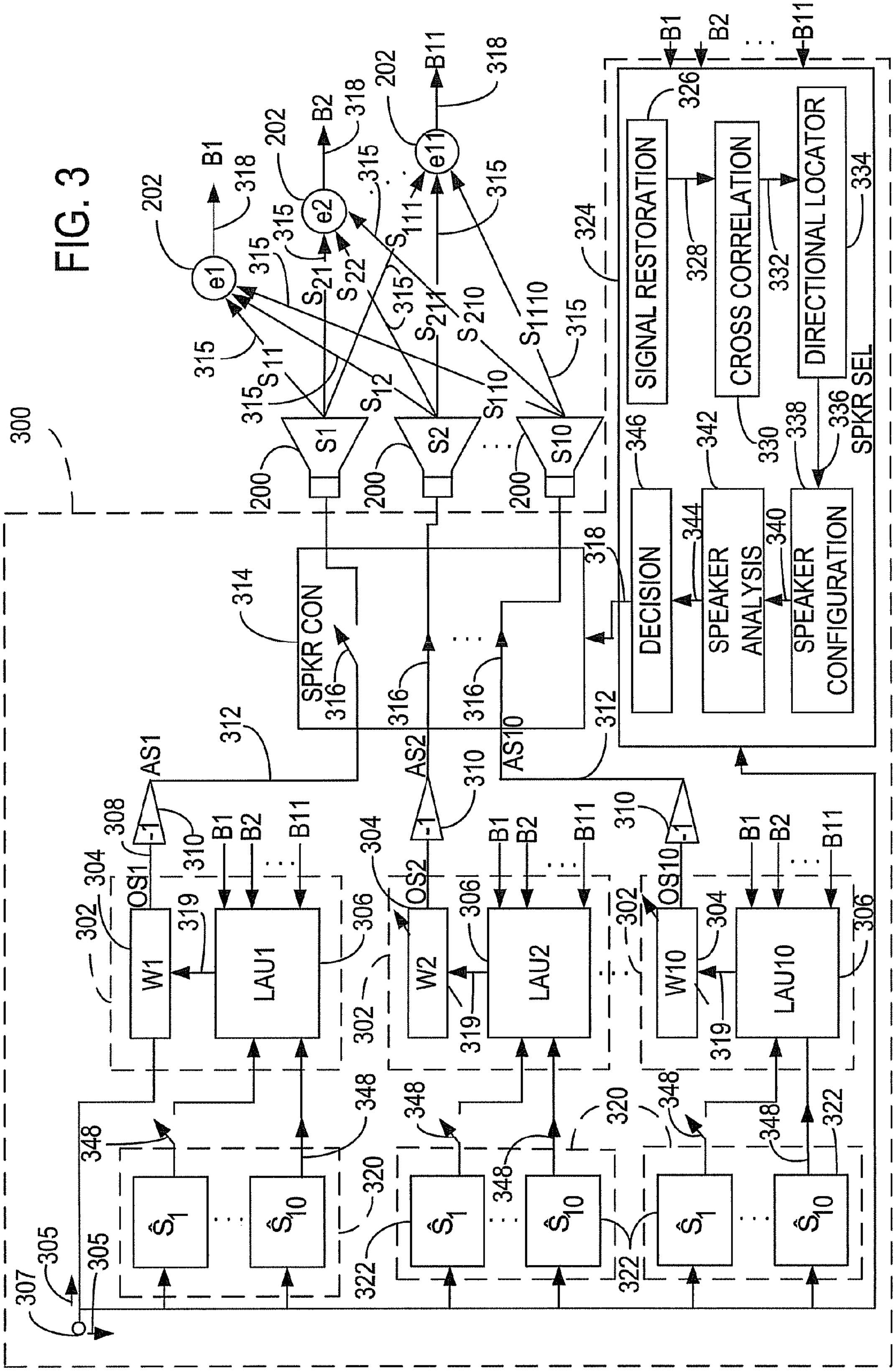
FIG. 3 is an example of a system implementing an ANC system configured to simulate anti-noise sound wave production.

FIG. 2 is a diagrammatic view of an example configuration of a plurality of speakers (Sn) 200 and a plurality of sensors, such as error microphones (em) 202, configured for use with an ANC system 300 (See FIG. 3). In FIG. 2 the plurality of speakers 200 include a first (S1) through tenth (S10) speaker and the plurality of error microphones (em) 202 may include a first (e1) through eleventh (e11) error microphone. Each error microphone (em) 202 may be associated with a respective quiet zone (Qm) 203. In other examples, an entire listening space may be a quiet zone containing multiple microphones (em) 202, or each of two or more quiet zones may include multiple microphones. The speakers (Sn) 200 may be used to produce anti-noise sound waves to destructively interfere with undesired sound X present in the quiet zones (Qm) 203 associated with each error microphone (em) 202.

Less than all of the speakers (Sn) 200 may be used at any one time to produce anti-noise sound waves configured to destructively interfere with undesired sound present in the quiet zones (Qm) 203. This "active speaker group," may be defined as particular speakers (Sn) 200 being actively being driven to produce anti-noise sound waves at any one time, may be adaptively selected during the production of anti-noise sound waves based on the location and characteristics of undesired sound. An active speaker group may include one or more speakers (Sn) 200. For example, in FIG. 2 speakers S1, S4, S6, and S9 may be selected as a first active speaker group 205. The first active speaker group 205 of speakers (Sn) 200 may be the only speakers currently selected to generate anti-noise sound waves. Various conditions related to undesired sound X may create a situation in which speakers (Sn) 200 other than those in the first active speaker group 205 may be better suited to produce anti-noise sound waves to cancel undesired sound X. As a result, a second active speaker group 207 may be selected. The second active speaker group 207 may be, for example, include speakers S1, S2, S6, and S7. In other examples, any combination of speakers may form any number of active speaker groups.

FIG. 3 is a block diagram of an example ANC system 300 configured for adaptive speaker selection that may be used with the example configuration of speakers (Sn) 200 and microphones (em) 202 shown in FIG. 2. In FIG. 3, the ANC system 300 is configured to generate anti-noise through the plurality of speakers (Sn) 200. The ANC system 300 is configured to determine the speakers 200 to be included in a current active speaker group. The ANC system 300 may include a plurality of anti-noise generator modules 302. Each anti-noise generator module 302 may include a respective adaptive filter (Wn) 304 and a respective learning algorithm unit (LAUn) 306. Each adaptive filter 304 receives an undesired sound signal 305 representative of undesired sound X. The undesired sound signal 305 may be generated by a sensor 307.

The sensor 307 may be configured to directly detect the undesired sound X. In one example, the sensor 307 may be a microphone configured to detect the actual undesired sound X. In other examples, the ANC system 300 may operate in a vehicle and sensor 307 may be an accelerometer configured to detect an undesired sound such as engine noise or road noise, for example, and generate the undesired sound signal 305 in response. In other examples, the undesired sound X may be simulated based on detected conditions within or outside of a listening area. The undesired sound X may also represent various undesired sounds. In one example, various sensors, such as the sensor 307, may be positioned within areas to detect undesired sounds such as within a motor vehicle to detect various undesired sounds associated with the motor vehicle. These undesired sounds may be aggregated as a single input signal such as the undesired sound signal 305. Anti-noise sound waves generated by the speakers (Sn) 200 may contain anti-noise sound waves configured to destructively interfere with each detected undesired sound or a dominant undesired sound present in the aggregate signal.

Each adaptive filter 304 may attempt to generate a respective output signal (OSn) 308 matching the undesired sound signal 305. The adaptive filter output signals (OSn) 308 may be inverted by a respective inverter 310; however each adaptive filter 304 may be configured to internally perform the signal inversion. Each output of the inverters 310 may be an anti-noise signal (ASn) 312. Each anti-noise signal (ASn) 312 may correspond to at least one of the speakers (Sn) 200 and may drive the corresponding speaker (Sn) 200 to produce sound waves including anti-noise. The ANC system 300 may include a speaker connection module 314. The speaker connection module 314 may be configured to selectively conduct each anti-noise signal (ASn) 312 to the corresponding speaker (Sn) 200 or to prevent the corresponding speaker (Sn) 200 from receiving the corresponding anti-noise signal (ASn) 312.

In FIG. 3, the speaker connection module 314 is illustrated as including switches 316 representing the ability of the speaker connection module 314 to selectively allow the each anti-noise signal (ASn) 312 to drive the corresponding speaker (Sn) 200. In alternative examples, various techniques may be implemented to selectively allow each speaker (Sn) 200 to be driven, such as disabling particular anti-noise generators 302. In other alternative examples, a single anti-noise generator 302 may be used in the ANC system 300. The single anti-noise generator 302 may generate a single anti-noise signal 312 that may be selectively received by the speakers (Sn) 200 through the speaker connection module 314.

The undesired sound X may be present in each of the quiet zones (Qm) 203 associated with each error microphone (em) 202. Each speaker (Sn) 200 may produce anti-noise sound waves to destructively interfere with an undesired sound X in each of one or more quiet zones (Qm) 203. Each error microphone (em) 202 may detect sound waves resulting from the combination of the anti-noise sound waves and the undesired sound X. Each speaker (Sn) 200 may have an associated secondary path ($S_{mn}$) 315 to each of the error microphones 202, where "m" represents the error microphone (em) 202 index and "n" represents the speaker (Sn) 200 index. For example, a secondary path 315 for speaker S1 may exist to each of the error microphones (em) 202. In FIG. 3, each secondary path 315 for the first, second, and tenth speakers S1, S2, and S10 are shown to each of first, second, and eleventh error microphones e1, e2, and e11.

Upon detection of sound waves, each error microphone (em) 202 may generate a respective error signal (Bm) 318. Each error signal (Bm) 318 is representative of the sound waves detected by the corresponding error microphone (em) 202. Sound waves resulting from the combination of anti-noise sound waves and the undesired sound X may be detected by each error microphone (em) 202. The error signals (Bm) 318 may be transmitted to ANC system 300.

The error signals (Bm) 318 and undesired sound X may be used to generate the anti-noise signals (ASn) 312. Each adaptive filter (Wn) 304 may receive the undesired sound signal 305. Each LAU (LAUn) 306 may receive the error signals (Bm) 318 and undesired sound signal 305 filtered by an estimated path filter module 320. Each LAU 306 may be configured to generate a respective update signal 319 provided to adjust filter coefficients associated with the respective adaptive filter (Wn) 304. Each LAU 306 may be configured to implement various learning algorithms, such as least mean squares (LMS), XLMS, NLMS, or other suitable learning algorithm.

Each estimated path filter module 320 includes an estimated path filter ($\hat{S}_n$) 322 for each speaker (Sn) 200. Each estimated path filter ($\hat{S}_n$) 322 is configured to estimate the physical secondary paths 315 a sound wave may traverse from each speaker (Sn) 200 to each of the error microphones (em) 202. For example, in FIG. 3, each speaker (Sn) 200 has a physical path to each of the error microphones (em) 200 resulting in ten estimated path filters ($\hat{S}_n$) 322 for each speaker (Sn) 200. The estimated path filters ($\hat{S}_n$) 322 may also reflect the effect of processing components with or outside the ANC system 300 that are traversed by signals used to generate the sound waves. The estimated path filters ($\hat{S}_n$) may be determined prior to initial activation of the ANC system 300. The estimated path filter ($\hat{S}_n$) 322 for each speaker (Sn) 200 may be represented as:

$$\hat{S}_n=\hat{S}_{1n}+\hat{S}_{2n}+\hat{S}_{3n}+\hat{S}_{4n}+\hat{S}_{5n}+\hat{S}_{6n}+\hat{S}_{6n}+\hat{S}_{7n}+\hat{S}_{8n}+\hat{S}_{9n}+\hat{S}_{10n}+\hat{S}_{11n} \qquad \text{(Eqn. 1)}$$

Where, for each estimated path $\hat{S}_{mn}$, "m" references the particular error microphone (em) 202 and "n" references the particular speaker (Sn) 200. Each estimated path filter (Sn) 322 will include similar estimated paths for each path from a particular speaker (Sn) 200 to a particular error microphone (em) 202.

The ANC system 300 may be configured to selectively drive fewer speakers (Sn) 200 to produce anti-noise sound waves than the number of speakers 200 available. The decision to drive fewer speakers 200 than available may be made for various reasons such as total processing power available, etc. The ANC system 300 may initially select a predetermined active speaker group, such as the active speaker group 205, to be driven to produce anti-noise sound waves. As conditions with respect to undesired sound targeted for cancellation change, inclusion of other speakers (Sn) 200 excluded from the initially-selected active speaker group may increase the accuracy of canceling undesired sound X in the quiet zones (Qm) 203. Inclusion of other speakers (Sn) 200 may also be desired in order to optimize cancellation of the undesired sound X.

The ANC system 300 may include a simulator module 324 as the speaker to perform speaker selection through simulated production of various anti-noise sound waves from various combinations of the speakers (Sn) 200. The simulator module 324 may be configured to internally generate the anti-noise generators 302 and associated anti-noise signals (ASn) 312 in order to simulate production of sound waves from the speakers (Sn) 200. The simulator module 324 may be configured to determine if an active speaker group should include additional or fewer speakers 200 or replace speakers 200 in the active speaker group with speakers 200 not currently in the active speaker group. The simulator module 324 may determine speaker combinations based on the error signal (Bm) 318 and the undesired sound signal X. The simulator module 324 may use information related to the anti-noise generator modules 302 to simulate generation of anti-noise signals 312 from the anti-noise generator modules 302.

The simulator module 324 may include various sub-modules used to determine particular speaker combinations. The simulator module 324 may include a signal restoration module 326 configured to determine an estimated undesired sound signal detected at each error microphone (em) 202. For example, error signal B1 is representative of sound waves detected by the error microphone e1. The signal B1 may be processed by the signal restoration module 326 to determine the state of the undesired sound X detected by the error microphone e1. Due to the different positions of the error microphones (em) 202 with respect to one another in the listening space, the undesired sound at each error microphone (em) 202 may be of a different state at each error microphone (em) 202 at a common point in time. The signal restoration module 326 may generate an estimated undesired sound signal 328 for each corresponding error signal 318. Each estimated undesired sound signal 328 may be provided to a cross-correlation module 330.

The cross-correlation module 330 may determine the position of each speaker (Sn) 200 relative to the source of undesired sound X and relative to the other speakers 200. In one example, a position of each speaker 200 may be represented as a point (Pn) (see FIG. 2) having three-dimensional Cartesian coordinates $(x_n,y_n,z_n)$ in the listening space. Each error microphone (em) 202 position may also be represented as Cartesian coordinates $(x_m,y_m,z_m)$ (not shown). However, other coordinate systems may be used to represent positions of the speakers 200 and the error microphones 202 in the listening space, such as polar, cylindrical, or other suitable coordinate system. The error microphones (em) 202 and speakers (Sn) 200 are all statically positioned relative to one another in a listening space. This relative positional relationship between the speakers (Sn) 200 and the error microphones (em) 202 allows one of the error microphones (em) 202 to be used as a reference point to solve for the position and direction of the source of undesired sound X.

The cross-correlation module 330 may be configured to select one of the error microphones 202 as a reference point. Upon selection of the error microphone 202 serving as the reference microphone, the error signal (Bm) 318 waveforms may be analyzed by the cross-correlation module 326. Referring to FIGS. 2 and 3, the cross-correlation module 326 may be configured to determine the position of the point Px (FIG. 2), which may be considered the source point of undesired sound X. A distance from the point Px to each error microphone (em) 202 may be represented as:

$$d_m = ct_m \quad \text{Eqn. (2)}$$

where $d_m$ is the distance from the source point Px to the particular error microphone (em) 202, c is the speed of the undesired sound X, and $t_m$ is the duration of time the undesired sound X travels from the source point Px to the particular error microphone (em) 202. In one example, the error microphone e2 may be selected as the reference point such that the Cartesian coordinate of the error microphone e2 is (0,0,0). The position of the source point Px may be represented as (x,y,z). For each error microphone (em) 202, Equation 2 may be represented as:

$$ct_m = \sqrt{(x-x_m)^2+(y-y_m)^2+(z-z_m)^2} \quad \text{(Eqn. 3)}$$

where $\sqrt{(x-x_m)^2+(y-y_m)^2+(z-z_m)^2}$ is $d_m$. In the case of the error microphone e2 serving as the reference microphone, Eqn. 2 may be represented as:

$$ct_2 = \sqrt{x^2+y^2+z^2} \quad \text{(Eqn. 4)}$$

Subtracting Equation 4 from Equation 3 for each error microphone (em) 202, except the reference error microphone e2 will produce:

$$c\Delta t_{m2} = \sqrt{(x-x_m)^2+(y-y_m)^2+(z-z_m)^2} - \sqrt{x^2+y^2+z^2} \quad \text{(Eqn. 5)}$$

where $\Delta t_{m2}$ is the time difference between the undesired sound arriving from the source point Px to the error microphones (em) 202 and the reference error microphone e2. Both sides of Equation 5 may be divided by "c" to isolate $\Delta t_{m2}$. Because the Cartesian coordinates for each error microphone (em) 202 known with respect to the reference error microphone e2 as the reference point, the Cartesian coordinates for the source point Px may be determined using Equation 5.

In alternative examples, some of the error microphones (em) 202 may be movable with respect to other error microphones (em) 202. For example, the ANC system 300 may be implemented in a vehicle. Some error microphones may be mounted in head rests of the vehicle. The head rests are connected to passenger and driver seats. The seat positions may be adjusted causing the positions of the error microphones (em) 202 to be adjusted as well. In such arrangements, the ANC system 300 may be configured to use a predetermined position for a particular error microphone (em) 202, such as the average position of the particular error microphone (em) 202 with respect to the total possible range of movement of the particular error microphone (em) 202.

Upon determination of the position of the source point Px, the cross-correlation module 330 may transmit an undesired noise position signal 332 to a directional locator module 334. Using the information from the undesired noise position signal 332, the directional locator module 334 may normalize the position (x,y,z) of the source point Px to determine the direction of the undesired sound X. The position of each speaker 200 $(x_n,y_n,z_n)$ is known due to the static position from the reference error microphone 202, such as the error microphone e2. The known relative position of the speaker 200 also allows a normal vector (Nn) 208 of each speaker 200 to be predetermined. Each normal vector (Nn) 208 represents a vector orthogonal from a planar surface from through which the sound waves produced from the particular speaker (Sn) 200 propagate, such as the face of each respective speaker (Sn) 200. Using the normal vector (Nn) 208 information and the position Pn of each speaker 200, the directional locator module 334 may determine the direction of the undesired sound the respect to the speakers 200. A positional information signal 336 may be generated by the directional locator module 334. The positional information signal 336 may include information regarding the direction of the undesired sound with respect to the position of the speakers 200.

The positional information signal 336 may be received by a speaker configuration module 338. The speaker configuration module 338 may determine at least one speaker 200 to add to the active speaker group or to replace particular speakers (Sn) 200 in the active speaker group. Using the directional information of the undesired sound X, the speaker configuration module 338 may determine that at least one speaker 200 not currently in the active speaker group may enhance cancellation of the undesired sound if used to generate anti-noise. In one example, the speaker configuration module 336 may determine a dot product of the normal vectors (Nn) 208 with the directional information of undesired sound.

In one example, speakers 200 having a normal vector (Nn) 208 planar, e.g. parallel to, to the direction of the undesired sound may be more desirable than speakers (Sn) 200 having normal vectors (Nn) 208 more orthogonal to the direction of the undesired sound X. The speaker configuration module 338 may determine which speakers (Sn) 200, if any, should be included in the active speaker group and if any speakers 200 currently in the active speaker group should be replaced. In one example, the speakers 200 (Sn) may be configured such that the number of speakers (Sn) 200 driven to produce anti-noise is fixed. Thus, any speakers 200 (Sn) not currently in the active speaker group selected by the speaker configuration module 3.38 would replace a speaker (Sn) 200 in the current group, such as that previously described with regard to the active speaker groups 205 and 207. In alternative examples, additional speakers (Sn) 200 may be included in the active speaker group without replacement of speakers (Sn) 200 currently in the active speaker group. The speaker configuration module 338 may also determine that speakers (Sn) 200 currently in the active speaker group may be removed from the active speaker group without the addition of another speaker (Sn) 200.

Upon determination of speakers (Sn) 200 to be included in the additional group, the speaker configuration module 338 may transmit a speaker configuration signal 340. The speaker configuration signal 340 may include information regarding the particular speakers (Sn) 200 selected by the speaker configuration module 338. The speaker configuration signal 340 may be transmitted to a speaker analysis module 342. The speaker analysis module 342 may be configured to perform simulations for the ANC system 300 to determine if speakers 200 selected by the speaker configuration module 338 may decrease error signals (Bm) 318 in at least one of the quiet zones (Qm) 203 if included in the active speaker group. The speaker analysis module 340 may use the error signals (Bm) 318, the undesired sound signal 305, and the estimated path filter module 320 to perform the simulations.

The speaker analysis module 342 may generate a simulation result signal 344. The simulation result signal 344 may include information regarding the results of simulations performed by the speaker analysis module 342. The simulation results signal 344 may be provided to a decision module 346. The decision module 346 may be configured to determine if the active speaker group should be reconfigured based on the simulation results signal 344. The decision module 346 may generate a speaker selection signal 348. The speaker selection signal 348 may include information regarding speakers 200 to be included or excluded from the active speaker group. The speaker selection signal 348 may be transmitted to the speaker connection module 314. The speaker connection module 314 may connect the speakers (Sn) 200 to be included in the active speaker group based on the speaker selection signal 348.

The estimated path filters ($\hat{S}_n$) 322 may be selectively used to filter the undesired sound signal 305 based on the corresponding speaker (Sn) 200 being driven to produce anti-noise sound waves. If a speaker (Sn) 200 is not selected as part of the active speaker group, the corresponding estimated path filter ($\hat{S}_n$) 322 should not be used to provide input to the anti-noise generators 302. For example, if speaker S1 is not in the current active speaker group, the undesired sound signal 305 should not be filtered by the estimated path filter $\hat{S}_1$ as an input to the LAUs 306. Switches 348 illustrated in the FIG. 3 represent that the estimated path filters ($\hat{S}_n$) 322 may be selectively implemented based on the corresponding speaker (Sn) 200 being included in the active speaker group.

In alternative examples, the simulator 324 may operate without use of the directional information. In such alternative examples, the simulator 324 may run various simulated combinations of speakers (Sn) 200 to determine if the active speaker group may be replaced with a different combination to more accurately generate anti-noise sound waves. In other alternative examples, the directional analysis provided through both the cross-correlation module 330 and the directional locator module 334 may be used without the use of the simulator to select active speaker groups. In such alternative examples, the directional information may be used to select other active speaker groups without the use of simulated results.

Figure 4:
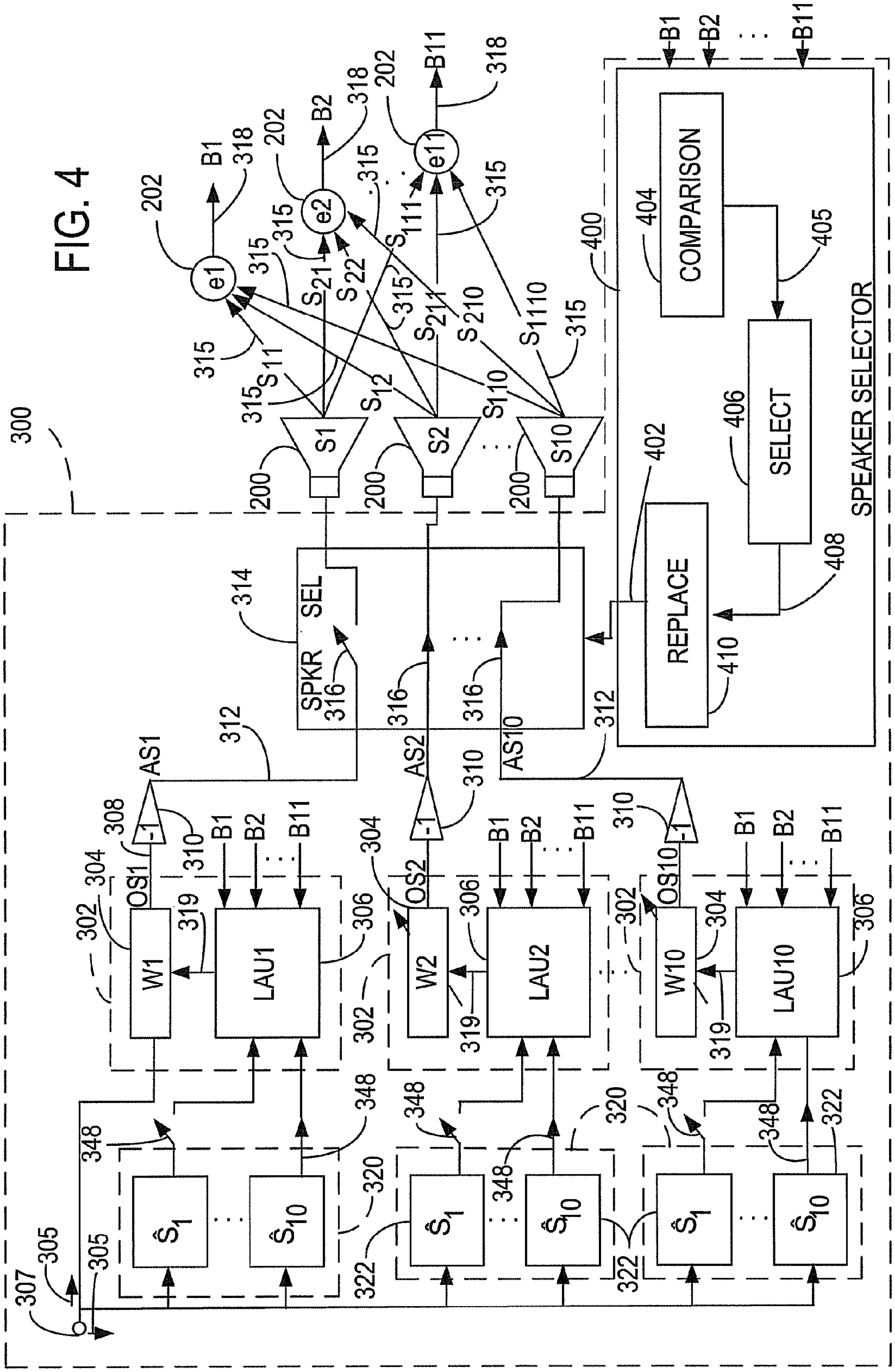
FIG. 4 is an example of a system implementing an ANC system.

FIG. 4 shows an alternative configuration for the ANC system 300. In FIG. 4, the ANC system 300 includes a speaker selection module 400 instead of the simulation module 324. The speaker selection module 400 may be configured to select at least one additional speaker (Sn) 200 at a time not in the current active group to produce anti-noise sound waves. The speaker selection module 400 may rotate production of anti-noise sound waves from each speaker (Sn) 200 not in the active group. Each speaker (Sn) 200 not in the active group may produce anti-noise sound waves for a predetermined amount of time. The simulation module 324 may generate a speaker selection signal 402 to the speaker connection module 314 to indicate which speakers (Sn) 200 should be currently producing anti-noise sound waves.

The speaker selection module 400 may receive the error signals (Bm) 318 produced by the error microphones (em) 202. The speaker selection module 400 may implement a comparison module 404. The comparison module 404 may compare the error signals (em) 404 resulting from anti-noise sound waves being generated by the active group of speakers (Sn) 200 to the error signals (Bm) 318 resulting from the addition of one or more speakers (Sn) 200 not in the active group.

As the comparison module 404 is comparing error signals, the speaker selection module 400 may continue to rotate particular speakers (Sn) 200 not in the active group to produce anti-noise sound waves along with the active group. As each non-active group speaker is selected, the comparison module 404 may determine if any of the error signals (Bm) 318 are reduced due to the addition of a non-active group speaker. The comparison module 404 may generate a comparison results signal 405. The comparison results signal 405 may include information a related to the error signal comparisons performed by the comparison module 404.

The speaker selection module 400 may include a selection module 406 that selects a particular non-active group speaker (Sn) 200 to include in the active group. For example, if anti-noise sound waves from two non-active group speakers (Sn) 200 reduce the error signals (em) 218, the selection module 404 may select the speaker (Sn) 200 responsible for a greater error signal reduction. Based on the comparison results signal 405, the selection module 404 may determine particular speakers (Sn) 200 to include in the active group as replacements for one or more speakers (Sn) 200 in the active group. Upon selection of a replacement speaker (Sn) 200, the selection module 406 may generate a selection signal 408. The selection signal 408 may include information regarding a particular speaker or speakers (Sn) 200 to include as a replacement to the active group of speakers (Sn) 200.

The speaker selection module 400 may include a replacement module 410. Once a replacement speaker (Sn) 200 has been identified to replace as speaker in the active group, the replacement module 410 may determine which active speakers (Sn) 200 should be replaced. In one example, the speaker selection module 400 may suspend producing anti-noise sound waves through non-active group speakers, once a replacement speaker (Sn) 200 has been selected. The speaker selection module 400 may remove each speaker (Sn) 200 in the active group individually while adding the replacement speaker (Sn) 200 to replace the removed speaker (Sn) 200. The replacement module 410 may monitor the error signals (Bm) 318 as each active group speaker (Sn) 200 is individually replaced. The lowest error signal (Bm) 318 may indicate that permanent replacement may provide more accurate noise cancellation. The speaker selection module 400 may provide the speaker selection signal 402 indicating the replacement speaker (Sn) 200 to be included in the active group.

The speaker selection module 400 may periodically determine if non-active group speakers (Sn) 200 are to be included in the active speaker group. In alternative examples, the replacement speaker (Sn) 200 may be added to the active speaker group without replacement of a current active group speaker (Sn) 200. In other alternative examples, non-active group speakers (Sn) 200 may be selected produce anti-noise sound waves during overlapping time periods. The speaker selection module 400 may select one or more of these non-active group speakers (Sn) 200 to replace speakers (Sn) 200 in the active speaker group or may be included in addition to current speakers (Sn) 200 in the active speaker group.

Figure 5:
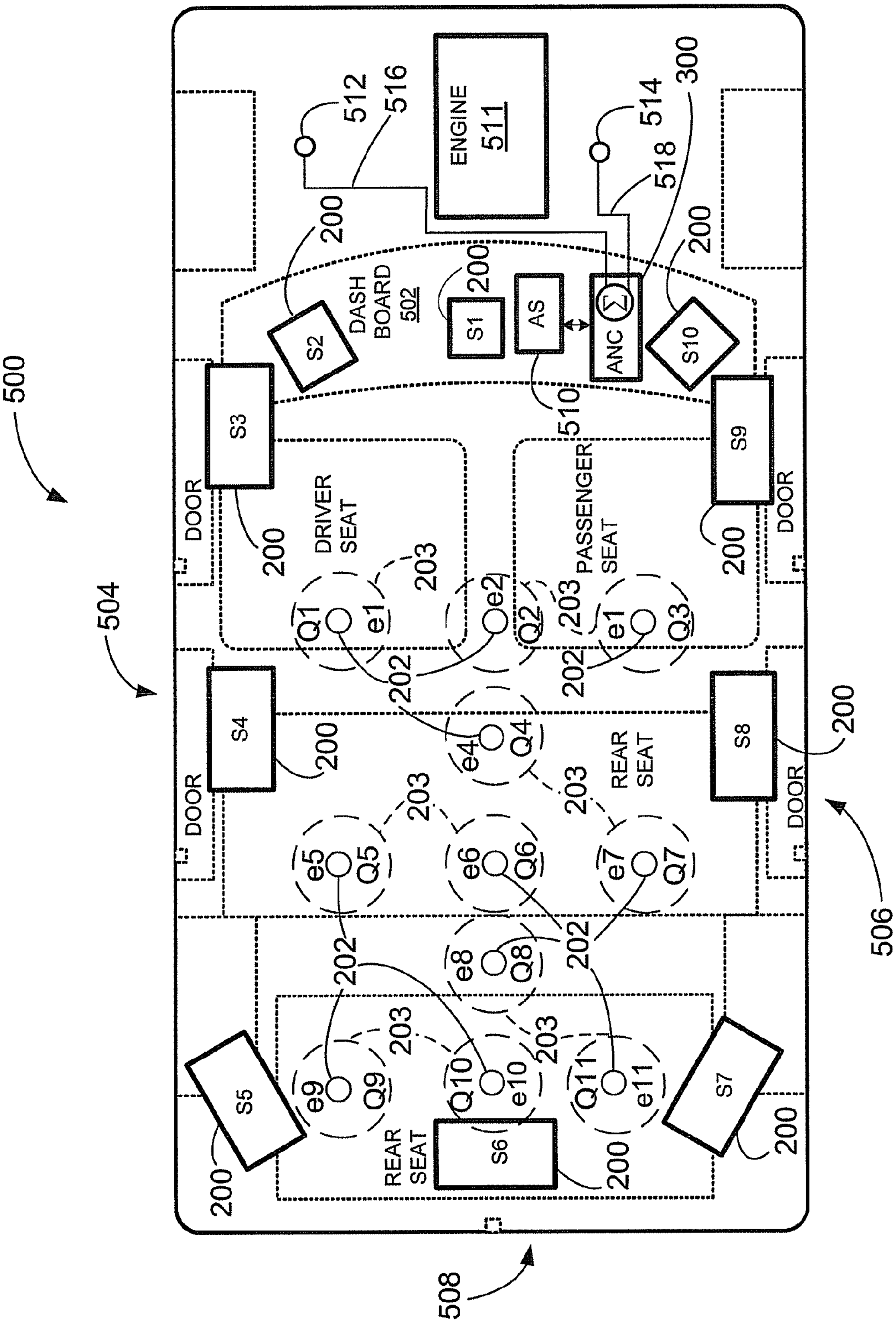
FIG. 5 is a top view of an example vehicle configured to implement the ANC systems of FIG. 3 and FIG. 4.

FIG. 5 shows an example of the ANC system 300 included in a vehicle 500. The speakers (Sn) 200 and the error microphones (em) 202 of FIG. 2 may be arranged in the vehicle 500 as shown in FIG. 5. The speakers (Sn) 200 and error microphones (em) 202 may be positioned in various arrangements within the vehicle 500. For example, the error microphones e1-e3, e5-e7, and e9-e11 may be mounted in head rests of the vehicle 500, while the error microphones e4 and e10 may be mounted on an interior surface of the vehicle 500, such as the roof. In FIG. 5, each microphone (em) 202 is shown as including a respective quiet zone (Qm) 203. In alternative embodiments, within the cabin of the vehicle 500, the ANC system 300 may be configured such that one quiet zone is generated including all or only some of the microphones (em) 200. In other alternative examples, several quiet zones may be generated, with each quiet zone including one or more microphones (em) 202.

The speakers (Sn) 200 may be positioned in various locations in the vehicle 500. For example, speakers S1, S2, and S10 may be positioned in the dashboard 502 of the vehicle. Speakers S2 and S3 may be positioned in the left side 504 of the vehicle 500 and speakers S8 and S9 may be positioned in the right side of the vehicle 506. Speakers S5 through S7 may be positioned in a rear area 508 of the vehicle 500. The ANC system 300 may be configured to operate with the speakers (Sn) 200 and the microphones (em) 202 as described with regard to FIG. 3. In FIG. 5, the ANC system 300 is shown as being in communication with an audio system (AS) 510. The ANC system 300 and audio system (AS) 510 may share the same speakers (Sn) 200.

As described with regard to FIGS. 2 and 3, undesired sound may originate from various sources such as engine noise from engine 504 of the vehicle 500, road noise, etc. Sensors 512 and 514 may be configured to detect undesired sound. In one example, the sensors 512 and 514 may be configured to detect different undesired sounds, such engine noise, fan noise, road noise or any other detectable undesired sound. The undesired sounds may be detected by the sensors 512 and 514, similar to the sensor 307, and may be converted to electrical signals transmitted via signal lines 516 and 518 to the ANC system 300. The signals through the signal lines 516 and 518 may be summed by the ANC system 300 for use in generating anti-noise signals (ASn) 312.

The sensors 512 and 514 may be microphones to detect the actual undesired sound. In one example, one or both of the sensors 512 and 514 may be accelerometers configured to detect engine noise from the engine 504. Any suitable sensor may be used to detect undesired sound. In other examples, any number of sensors, such as the sensors 512 and 514 may be used to detect undesired sound. In alternative or additional examples, at least one or more of the undesired sounds may be simulated to produce signals such as the signals transmitted through the signal lines 516 and 518.

In operation, as previously described, the ANC system 300 may generate anti-noise signals 312 to drive the speakers (Sn) 200. In one example, particular speakers (Sn) 200 may not be used for production of anti-noise sound waves, such as high-frequency speakers, or "tweeters," while some of the speakers may always be used for anti-noise sound wave production such as low frequency speakers, or "sub-woofers."

In one example, the ANC system 300 may be configured to drive an active speaker group of speakers smaller in number than the total number of speakers (Sn) 200 available in the vehicle 500. The speakers (Sn) 200 included in the active speaker group may be adaptively selected by the ANC system 300 based in manners described with regard to FIGS. 3 and 4. For example, if the sensors 512 and 514 are configured to detect different undesired sounds, the undesired sounds may appear at different times and intensities. Thus, in one example, the ANC system 300 would select a first active speaker group and based on the change in the undesired sounds may select different speakers (Sn) 200 to be included in the active speaker group additionally, or may replace a speaker (Sn) 200 in the active speaker group with a speaker (Sn) 200 not in the active speaker group. This automatic adjustment of the speaker combinations may be performed routinely during operation of the ANC system 300.

Figure 6:
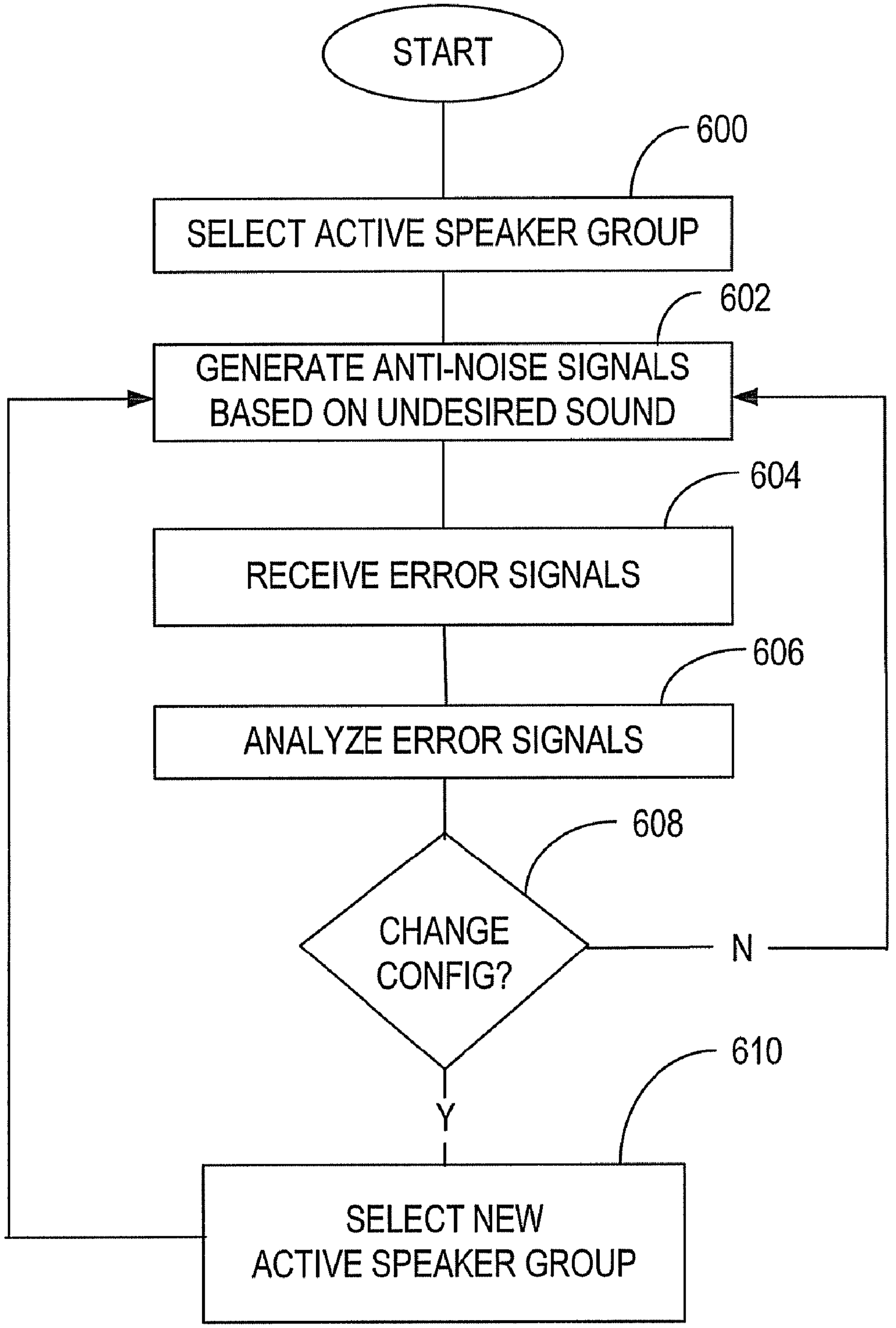
FIG. 6 is an example operational flow diagram of the ANC system of FIG. 3.

FIG. 6 shows an example flow diagram illustrating operation of the ANC system 300 in with reference to FIGS. 2, 3, and 4. The operation begins at block 600 upon initialization of the ANC system 300. At block 600, the ANC system 300 may select an active speaker group, such as the active speaker group 205. In one embodiment, selection of the active speaker group 205 may be predetermined such that upon each initialization the active speaker group 203 is initially selected by the ANC system 300. In another example, the ANC system 300 may monitor undesired sound as a basis to select an initial active speaker group of speakers (Sn) 200. At block 602, the ANC system 300 may generate anti-noise signals 312 based on the undesired sound signal 305 and error signals (Bm) 318. Upon initialization of the ANC system 300, the ANC system 300 may begin generating anti-noise signals 312 based on predetermined coefficients for each adaptive filter (Wn) 304. The error microphones (em) 202 may begin to detect sound in the one or more respective quiet zones (Qm) 203 and transmit error signal (Bm) 318 to the ANC system 300.

At block 604, the ANC system 300 may receive error signals resulting from a combination of anti-noise sound waves produced by the speakers (Sn) 200 in the active speaker group and the undesired sound in one or more quiet zones (Qm) 203. At block 606, the ANC system 300 may analyze the error signals. The ANC system 300 may analyze the error signals in various manners depending on the particular configuration. For example, if the ANC system 300 is implement simulation module 324 of FIG. 3, both directional and simulation analyses may be performed. In another example, the speaker selection module 400 of FIG. 4 may be implemented using real-time information based on the use of additional speakers used to produce anti-noise sound waves.

At block 608, the ANC system 300 may determine if the active speaker group configured is to be changed. If the active speaker group is not to be changed, the operation may return to block 602. If the configuration is to be changed, at block 610 a new active speaker group is selected and the operation may return to block 602.

Figure 7:
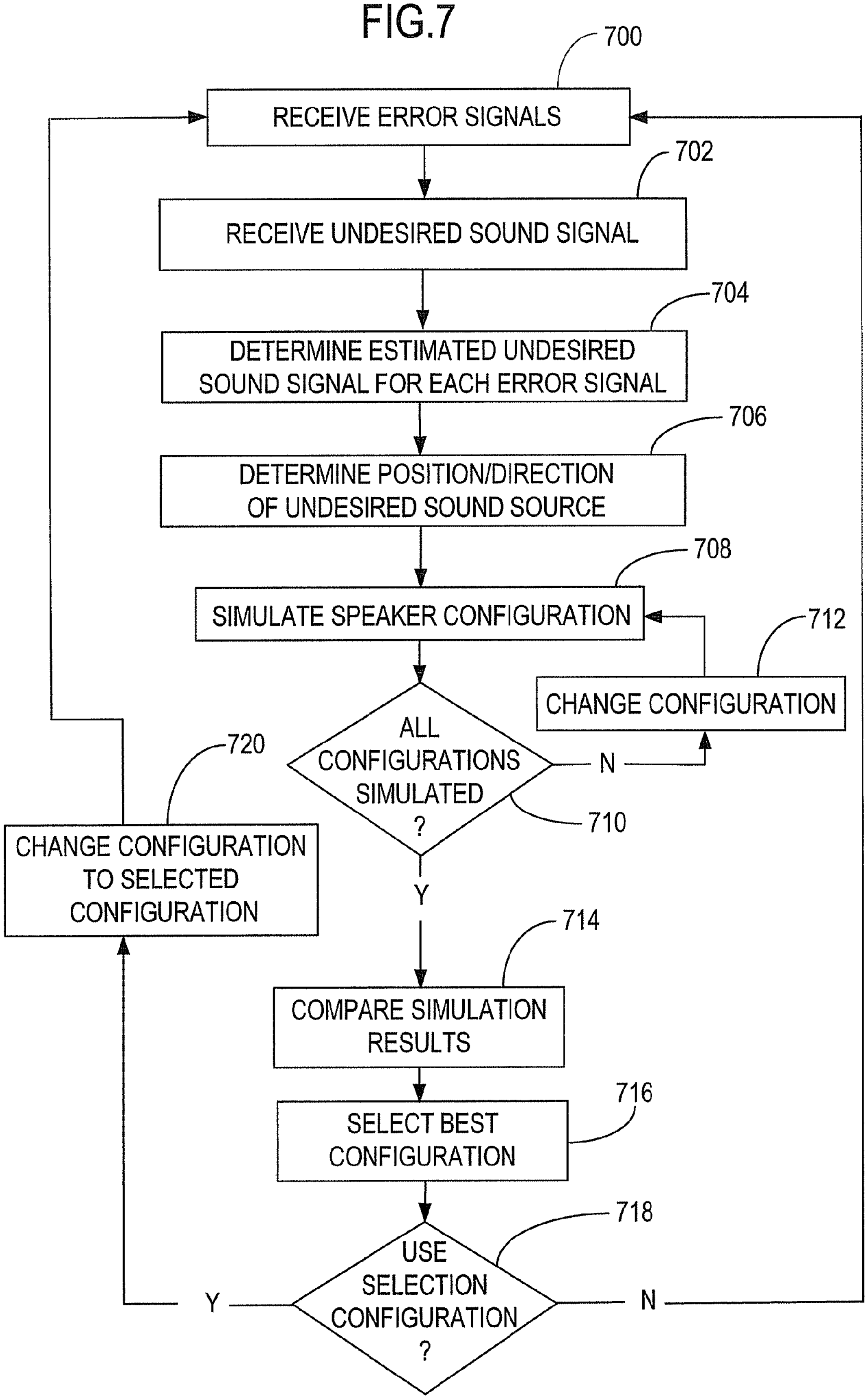
FIG. 7 is an example operational flow diagram of a simulation module implemented by the ANC system of FIG. 3.

FIG. 7 shows an example flow diagram illustrating operation of the simulator module 324 in with reference to FIGS. 2 and 3. At block 700, the simulator 324 may receive the error signals (Bm) 318 generated by the error microphones (em) 202. At block 702, the simulator module 324 may receive the undesired sound signal 305. At block 704, the simulator module 324 may determine the estimated undesired sound signal 328 for each error microphone (em) 202. In one example, the simulator module 324 may implement the signal restoration module 326 to determine the estimated undesired sound signal 328 for each error microphone (em) 202.

At block 706, the simulator module 324 may determine a position and direction of an undesired sound source. In one example, the simulator module 324 may implement the cross-correlation module 330 and the direction locator module 334 to determine the source point and direction of the undesired sound X. At block 708, the simulator module 324 may simulate various speaker combinations. In one example, the simulator module 324 may simulate speaker combinations other than the current active speaker group. The simulation may be performed by the speaker configuration module 338. Each possible combination may be simulated at block 708. At block 710 a determination is made as to if each desired possible combination has been simulated. If not, at block 712 the combination may be changed and the simulation ran for the new combination. Once all desired combinations have been simulated, at block 714 the combination simulation results may be compared to one another. At block 716 the "best" simulated speaker combination may be selected. The "best" simulated speaker combination may be the combination that simulates the most superior cancellation of the undesired sound X as compared to the other simulated speaker combinations. In one example, the selection at block 716 may be performed by the speaker analysis module 342. At block 718 a comparison of the "best" simulated speaker combination may be made to the current performance of the active speaker group. The comparison at block 718 may be performed by the decision module 346. If the simulated combination is determined to not provide superior performance compared to the active speaker group, the operation may return to block 700 to continue operation of the simulation module 324. If the simulated combination is determined to provide superior performance, at block 720 the active speaker group may be changed to the speakers (Sn) 200 included in the simulated combination to form a new active speaker group. Upon changing to this new active speaker group, the operation may return to block 700.

Figure 8:
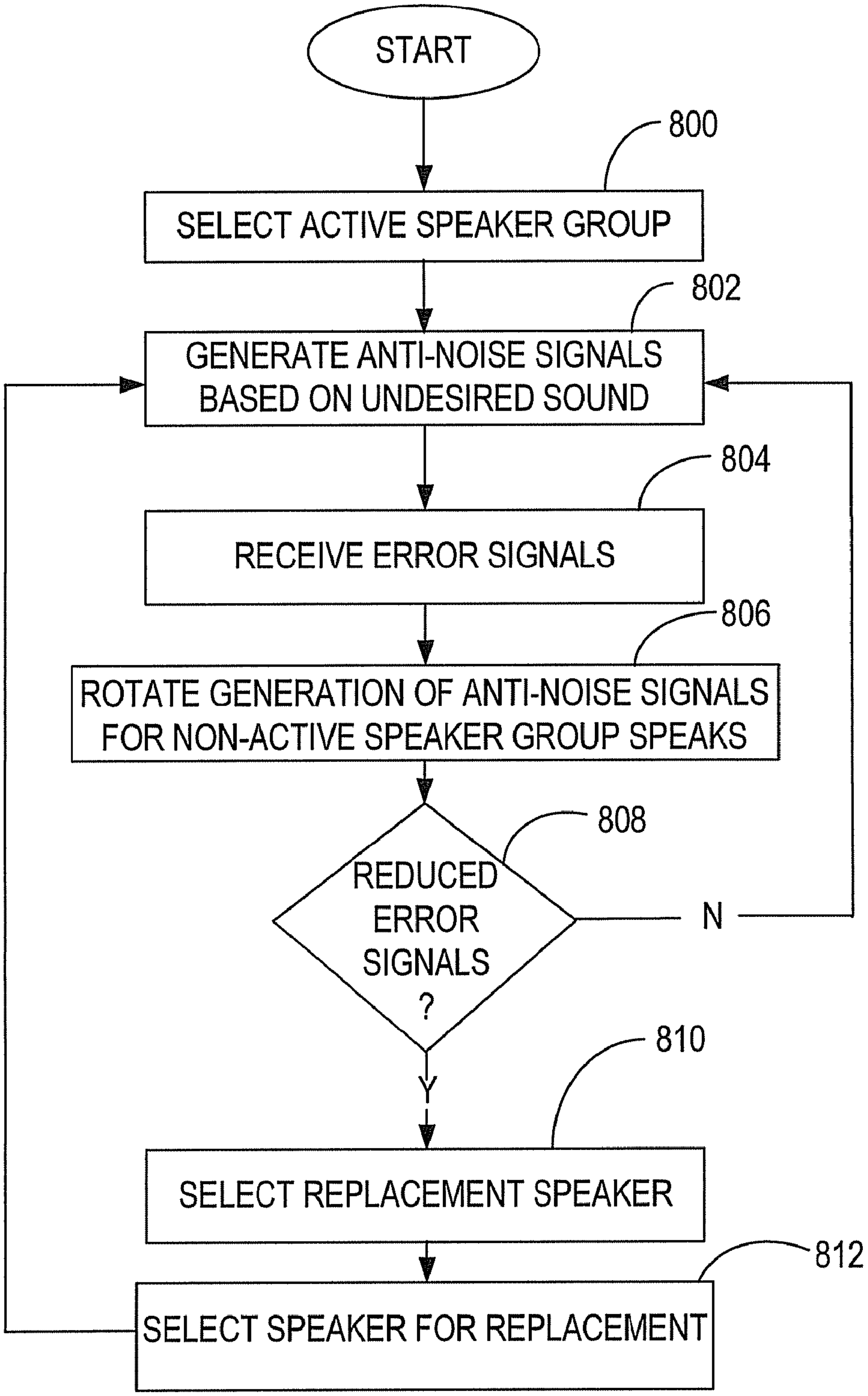
FIG. 8 is an example operational flow diagram of the ANC system of FIG. 4.

FIG. 8 is an example flow diagram of operating the ANC system 300 of FIG. 4. The operation begins at block 800 upon initialization of the ANC system 300. At block 800, the ANC system 300 may select an active speaker group, such as the active speaker group 205. In one example, selection of the active speaker group 205 may be predetermined such that upon each initialization the active speaker group 205 is initially selected by the ANC system 300. In another example, the ANC system 300 may monitor undesired sound as a basis to select an initial active speaker group of speakers (Sn) 200. At block 802, the ANC system 300 may generate anti-noise signals 312 based on the undesired sound signal 305 and error signals (Bm) 318. Upon initialization of the ANC system 300, the ANC system 300 may begin generating anti-noise signals 312 based on predetermined coefficients for each adaptive filter (Wn) 304. The error microphones (em) 202 may begin to detect sound in the one or more respective quiet zones (Qm) 203 and transmit error signal (Bm) 318 to the ANC system 300. At block 804, the ANC system 300 may receive the error signals (Bm) 318.

At block 806, the ANC system 300 may rotate anti-noise production of sound waves from non-active group speakers (Sn) 200. The ANC system 300 may implement the speaker selection module 400. The speaker selection module 400 may select one or more speakers (Sn) 200 not in the active speaker group to produce anti-noise sound waves. Each non-active speaker group speaker (Sn) 200 may be selected to produce anti-noise sound waves for a predetermined amount of time, such as less than 10 seconds.

At block 808, the ANC system 300 may determine if any of the error signals (Bm) 318 are reduced when one of the non-active speaker group speakers (Sn) 200 are included in the active speaker groups. If not error signal reduction occurs, the operation may return to block 802. If error signal reduction occurs, at block 810 the speaker selection module 400 of the ANC system 300 may determine which non-active speaker group speaker (Sn) 200 may replace one of the current speakers (Sn) 200 in the active speaker group. In one example, the ANC system may select the speaker (Sn) 200 providing the most error reduction as compared the other non-active group speakers (Sn) 200 to replace a speaker (Sn) 200 in the active speaker group.

Once the replacement speaker (or speakers) (Sn) 200 is selected, at block 812, the ANC system 300 may determine a particular speaker (Sn) 200 in the active speaker group to be replaced. In one example, the speaker selection module 400 may suspend rotating production of anti-noise sound waves with the non-active speaker group. The speaker selection module 400 may remove active speaker group speakers (Sn) 200 and replace them one-by-one with the speaker or speakers (Sn) 200 identified at block 810. The speaker selection module 400 may monitor the error signals (Bm) 318 as each active speaker group speaker (Sn) 200 is replaced by the replacement speaker for a predetermined amount of time. The speaker combination providing the lowest error signal may be selected as the new active speaker group that includes the replacement speaker. The operation may return to block 802.

Figure 9:
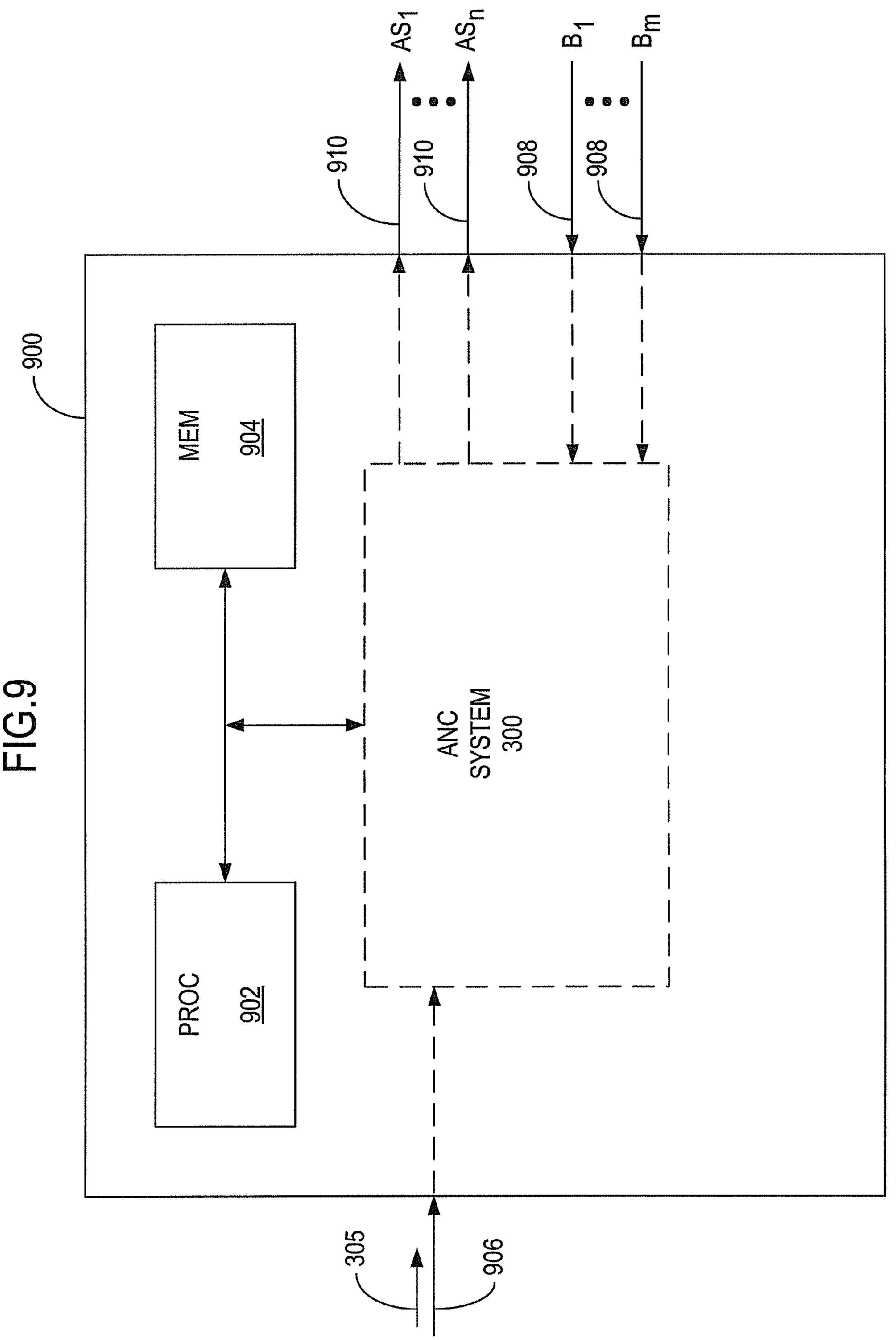
FIG. 9 is a block diagram of an example computer device configured to operate the ANC systems of FIGS. 3 and 4.

FIG. 9 is a block diagram of a computer device 900 configured to execute the ANC system 300. The computer device 900 may include processor 902 and a memory 904. The ANC system 300 may be implemented as logic on the computer device 902 or may be stored as a plurality of executable instructions on the memory 902. The computer device 900 may be configured to operate the ANC system 300. In one example, the computer device 900 may be configured to receive the undesired error signal 305 through a signal line 906. The computer device 900 may also be configured to receive the error signals (Bm) 318 through the signal lines 908. The undesired error signal 305 and error signals (Bm) 318 may be implemented by the ANC system 300 as discussed with regard to FIGS. 2 through 4. The computer device 900 may also be configured to transmit the anti-noise signals (ASn) 312 through signal lines 910 to speakers (Sn) 200 (not shown) included in the active speaker group.

In one example, the memory 904 may include one or more memories, be computer-readable storage media or memories, such as a cache, buffer, RAM, removable media, hard drive or other computer readable storage media. Computer readable storage media include various types of volatile and nonvolatile storage media. Various processing techniques may be implemented by the processor 902 such as multiprocessing, multitasking, parallel processing and the like, for example. The processor 902 may include one or more processors configured to operate the ANC system 300.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. An active noise control system comprising:

a memory in communication with a processor;

where the processor is configured to select a first speaker group from a plurality of speakers, where the first speaker group is selected to receive a corresponding anti-noise signal configured to drive the first speaker group to produce sound waves to destructively interfere with an undesired sound present in at least one quiet zone;

the processor further configured to receive a first error signal, where the first error signal is representative of a combination of sound waves produced by the first speaker group and the undesired sound detected in the at least one quiet zone;

the processor further configured to determine when a second speaker group different than the first speaker group is configured to produce a second error signal less than the first error signal, where the second error signal is representative of a combination of sound waves produced by the second speaker group and the undesired sound detected in the at least one quiet zone; and the processor further configured to replace the first speaker group with the second speaker group.

2. The active noise control system of claim 1, where the processor is further configured to select at least one speaker not included in the first speaker group to receive a corresponding anti-noise signal configured to drive the at least one speaker for a predetermined amount of time to produce sound waves to destructively interfere with the undesired sound present in the at least one quiet zone.

3. The active noise control system of claim 2, where the processor is configured to receive a third error signal, where the third error signal is representative of a combination of sound waves produced by the at least one speaker, the first speaker group, and the undesired sound detected in the at least one quiet zone.

4. The active noise control system of claim 3, where the processor is configured to select the at least one speaker to replace a first speaker in the first speaker group to form the second speaker group when said third error signal is less than the first error signal.

5. The active noise control system of claim 1, where the processor is further configured to simulate sound wave production by the second speaker group based on a signal representative of the undesired sound and the first error signal;

the processor further configured to determine a first simulated error signal based on the simulated sound wave production.

6. The active noise control system of claim 5, where the processor is further configured to replace the first speaker group with the second speaker group when the first simulated error signal is less than the first error signal.

7. The active noise control system of claim 1, where the first error signal is a plurality of error signals, where each error signal is produced by an error sensor, where each error sensor is positioned within a respective quiet zone, and where the processor is further configured to correlate a relative speaker position for each of the plurality of speakers and a relative error sensor position for each of the plurality of error sensors.

8. The active noise control system of claim 7, where the processor is further configured to determine a direction of the undesired sound based on the relative speaker positions and the relative error sensor positions.

9. The active noise control system of claim 8, where the processor is further configured to select the second speaker group based on the direction of the undesired sound.

10. The active noise control system of claim 9, where the processor is configured to select at least one speaker to be included in the second speaker group, where the direction of the undesired sound is more planar with sound waves produced by the at least one speaker to be included in the second speaker group than with at least one speaker included in the first speaker group.

11. A method of operating an active noise control system, the method comprising:

selecting a first speaker group from a plurality of speakers with a processor, where the first speaker group is selected to receive a corresponding anti-noise signal configured to drive the first speaker group to produce sound waves to destructively interfere with an undesired sound present in at least one quiet zone;

receiving a first error signal with the processor, where the first error signal is representative of a combination of sound waves produced by the first speaker group and the undesired sound detected in the at least one quiet zone;

determining with the processor when a second speaker group different than the first speaker group is configured to produce a second error signal less than the first error signal, where the second error signal is representative of a combination of sound waves produced by the second speaker group and the undesired sound detected in the at least one quiet zone; and the processor replacing the first speaker group with the second speaker group.

12. The method of claim 11, where the processor is further configured to simulate sound wave production by the second speaker group based on a signal representative of the undesired sound and the first error signal;

the processor further configured to determine a first simulated error signal based on the simulated sound wave production.

13. The method of claim 12 further comprising:

simulating production of sound waves from a third speaker group with the processor, where the third speaker group is the first speaker group with an exclusion of at least one speaker from the first speaker group;

determining a second simulated error signal with the processor based on the simulated production of sound waves from the third speaker group;

comparing the first simulated error signal to the second simulated error signal with the processor; and selecting one of the second speaker group or the third speaker group with the processor to replace the first speaker group based on the comparison of the first simulated error signal and the second simulated error signal.

14. The method of claim 13, further comprising:

the processor replacing the first speaker group with the second speaker group based on the first simulated error signal when the second speaker group is selected; and the processor replacing the first speaker group with the third speaker group based on the second simulated error signal when the third speaker group is selected.

15. The method of claim 12, further comprising:

simulating production of sound waves from a third speaker group with the processor, where the third speaker group is different from the first speaker group and the second speaker group, where the simulated production of sound waves from the third speaker group is based on the first error signal and the signal representative of the undesired sound;

determining a second simulated error signal based on the simulated production of sound waves from the third speaker group with the processor;

the processor comparing the first simulated error signal to the second simulated error signal; and selecting one of the second speaker group or the third speaker group with the processor to replace the first speaker group based on the comparison of the first simulated error signal and the second simulated error signal.

16. The method of claim 15, further comprising:

replacing the first speaker group with the second speaker group based on the first simulated error signal when the second speaker group is selected; and replacing the first speaker group with the third speaker group based on the second simulated error signal when the third speaker group is selected.

17. The method of claim 15, where simulating sound wave production by the second speaker group comprises simulating sound wave production by the second speaker group from the plurality of speakers, where the second speaker group includes at least one speaker included in the first speaker group.

18. A computer-readable medium comprising a plurality of instructions executable by a processor to operate an active noise control system, the computer-readable medium comprising:

instructions to select a first speaker group from a plurality of speakers, where the first speaker group is selected to receive a corresponding anti-noise signal configured to drive the first speaker group to produce sound waves to destructively interfere with an undesired sound present in at least one quiet zone;

instructions to receive a first error signal, where the first error signal is representative of a combination of sound waves produced by the first speaker group and the undesired sound detected in the at least one quiet zone;

instructions to determine when a second speaker group different than the first speaker group is configured to produce a second error signal less than the first error signal, where the second error signal is representative of a combination of sound waves produced by the second speaker group and the undesired sound detected in the at least one quiet zone; and instructions to replace the first speaker group with the second speaker group.

19. The computer-readable medium of claim 18 further comprising instructions to select each of the speakers not included in the first speaker group to receive a corresponding anti-noise signal configured to drive the each of the respective speakers for a predetermined amount of time to produce sound waves to destructively interfere with the undesired sound present in the at least one quiet zone.

20. The computer-readable medium of plain 19 further comprising instructions to receive a respective temporary error signal for the each of the speakers not included in the first speaker group, where each respective temporary error signal is representative of a combination of sound waves produced by the each of the respective speakers not included in the first speaker group, the first speaker group, and the undesired sound detected in the at least one quiet zone.

21. The computer-readable medium of claim 20, further comprising instructions to select a replacement speaker to include in the second speaker group, where the replacement each of the speakers not included in the first speaker group having a lowest temporary error signal relative to other temporary error signals.

22. The computer-readable medium of claim 21, further comprising instructions to replace a speaker included in the first speaker group with the replacement speaker.

* * * * *

UNITED STATES PATENT AND TRADEMARK OFFICE

CERTIFICATE OF CORRECTION

PATENT NO. : 8,077,873 B2
APPLICATION NO. : 12/466282
DATED : December 13, 2011
INVENTOR(S) : Vasant Shridhar et al.

It is certified that error appears in the above-identified patent and that said Letters Patent is hereby corrected as shown below:

Column 20, Line 29:

After "replacement" insert --speaker is the respective--

Signed and Sealed this
Fourteenth Day of February, 2012

David J. Kappos
*Director of the United States Patent and Trademark Office*

UNITED STATES PATENT AND TRADEMARK OFFICE

CERTIFICATE OF CORRECTION

PATENT NO. : 8,077,873 B2
APPLICATION NO. : 12/466282
DATED : December 13, 2011
INVENTOR(S) : Shridhar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 356 days.

Signed and Sealed this
Tenth Day of April, 2012

David J. Kappos

David J. Kappos
*Director of the United States Patent and Trademark Office*